US008658411B2

(12) United States Patent  (10) Patent No.: US 8,658,411 B2
Irie et al.  (45) Date of Patent: Feb. 25, 2014

(54) METHOD OF TREATING WASTEWATER CONTAINING ORGANIC COMPOUND

(75) Inventors: Ryozo Irie, Ina (JP); Michio Tabata, Gifu (JP); Yoshihisa Hibi, Yorogun (JP)

(73) Assignee: Ibiden Co., Ltd., Ogaki-shi (JP)

( * ) Notice: Subject to any disclaimer, the term of this patent is extended or adjusted under 35 U.S.C. 154(b) by 1698 days.

(21) Appl. No.: 11/721,631

(22) PCT Filed: Apr. 21, 2006

(86) PCT No.: PCT/JP2006/008416
§ 371 (c)(1),
(2), (4) Date: Jun. 13, 2007

(87) PCT Pub. No.: WO2006/115199
PCT Pub. Date: Nov. 2, 2006

(65) Prior Publication Data
US 2010/0044304 A1 Feb. 25, 2010

(30) Foreign Application Priority Data

Apr. 21, 2005 (JP) .................. 2005-124124
May 26, 2005 (JP) .................. 2005-154525
May 26, 2005 (JP) .................. 2005-154530

(51) Int. Cl.
*C12N 1/00* (2006.01)
(52) U.S. Cl.
USPC ............. 435/243; 435/244; 435/7.1; 435/252
(58) Field of Classification Search
None
See application file for complete search history.

(56) References Cited

U.S. PATENT DOCUMENTS

| 4,356,092 | A | 10/1982 | Shimizu et al. |
|---|---|---|---|
| 4,511,657 | A | 4/1985 | Colaruotolo et al. |
| 5,079,166 | A | 1/1992 | Winter et al. |
| 5,314,821 | A | 5/1994 | Tyndall |
| 5,532,162 | A | 7/1996 | Aamot |
| 5,614,098 | A | 3/1997 | Shao et al. |
| 5,888,396 | A | 3/1999 | Perriello |
| 6,051,130 | A | 4/2000 | Perriello |
| 6,083,404 | A | 7/2000 | Sommese et al. |
| 6,156,203 | A | 12/2000 | Anthony |
| 6,245,235 | B1 | 6/2001 | Perriello |
| 2004/0166576 | A1 | 8/2004 | Sadaie et al. |
| 2008/0145917 | A1 | 6/2008 | Garcia et al. |

FOREIGN PATENT DOCUMENTS

| CN | 1222498 | 7/1999 |
|---|---|---|
| EP | 0095049 | 11/1983 |
| EP | 0274856 | 7/1988 |
| EP | 0463902 | 1/1992 |
| EP | 0650931 | 5/1995 |
| EP | 1224965 | 7/2002 |
| JP | S51-082781 | 7/1976 |
| JP | H02-261390 | 10/1990 |
| JP | H04-268000 | 9/1992 |
| JP | H06-170387 | 6/1994 |
| JP | H07-100483 | 4/1995 |
| JP | H09-075977 | 3/1997 |
| JP | 9-187779 | 7/1997 |
| JP | H10-296287 | 11/1998 |
| JP | H11-19675 | 1/1999 |
| JP | 2001-198591 | 7/2001 |
| JP | 2001-259686 | 9/2001 |
| JP | 2002-086181 | 3/2002 |
| JP | 2002-301494 | 10/2002 |
| JP | 2003-089899 | 3/2003 |
| JP | 2003-164862 | 6/2003 |
| JP | 2003-181490 | 7/2003 |
| JP | 2003-334588 | 11/2003 |
| JP | 2004-248618 | 9/2004 |
| JP | 2005-76103 | 3/2005 |
| TW | 509663 | 11/2002 |
| WO | WO 92/19373 | 11/1992 |
| WO | 98/27015 | 6/1998 |
| WO | WO 03/011487 A1 | 2/2003 |
| WO | 2004/071969 | 8/2004 |
| WO | 2004/101449 | 11/2004 |

OTHER PUBLICATIONS

Seiler et al. (European J. Appl. Microbiol. Biotechnol. (1982), vol. 14, pp. 97-104).*
Mach et al. (American Society for Microbiology, 1982, vol. 44, No. 6, pp. 1395-1403).*

(Continued)

*Primary Examiner* — Hope Robinson
(74) *Attorney, Agent, or Firm* — Ditthavong Mori & Steiner, P.C.

(57) ABSTRACT

The problem addressed by the present invention is to provide a method of treating an organic substance-containing waste liquid, and a treatment apparatus therefor, and an additive for treating an organic substance-containing waste liquid, and a bacterium for degrading an organic substance component or the like in the waste liquid, capable of accomplishing at least one of treatment of the organic substance-containing waste liquid with a high efficiency and a high treatment rate, without substantially generating a foul odor, and obtainment of water quality that is suitable for releasing to sewage, a public water area, or the like. This problem is solved by providing a method of treating an organic substance-containing waste liquid characterized by contacting an activated sludge containing a specified bacterium with an organic substance-containing waste liquid. The invention also provides a treatment apparatus therefor and an additive for treating an organic substance-containing waste liquid which is used by adding the additive to an activated sludge in a treatment tank in which a specified bacterium is present, and a specified bacterium for degrading an organic substance-containing waste liquid.

14 Claims, 2 Drawing Sheets

(56) References Cited

OTHER PUBLICATIONS

Kim et al. (International J. of Systemic and Evolutionary Microbiology, vol. 56, 2006, pp. 2031-2036).*

R.J. Seviour et al., "The Microbiology of Activated Sludge". Published by Kluwer Academic Publishers, 99-121, 147-202, 1999.

Ryozo Iriye et al., "Studies on the Improvement of Sewage Treatment by Increasing/Dominating *Bacillus* spp". Journal of Antibacterial and Antifungal Agents, 1999, vol. 27, No. 7, 431-440 (English abstact included).

Yuzuru Kimochi et al., "Yuyo Shoka Saikin *Alcaligenes faecalis* no Donyu ni yoru Chisso Jokoyo Process no Kodoka", Seibutsu Riyo Shingijutsu Kenkyu Symposium Ronbunshu, 2000, vol. 7, 126-130 (English tanslation included).

Helga Blaim et al., "Microbial Population in an Activated Sludge Treatment Plant of a Chemical Combine". Zeotschrift Fuer Wasser- und Abwasser-Forschung, 1984, vol. 17, No. 2, 37-39, 41.

Huang J.S. et al., Effect of addition of *Rhodobactor* sp. to activated-sludge reactors treating piggery wastewater. Water research, (Nov. 2001), vol. 35, No. 16, pp. 3867-3875.

H Melasniemi et al., "Comparative Analysis of Biological Phosphate Removal (BPR) and non-BPR Activated Sludge Bacterial Communities with Particular Reference to *Acinetobacter*". Journal of Industrial Microbiology and Biotechnology, Dec. 1998, vol. 21, No. 6, 300-306.

Teizi Urakami et al., "Isolation and Identification of N, N-Dimethylformamide Biodegrading Bacteria" J. Ferment Bioeng., 1990, vol. 70, No. 1, 45-47.

Shinya Nakamoto et al., "Biseibutsu o Riyo sita Haisui Shori Gijutsu" NEC Technical Journal, 1993, vol. 46, No. 9, 39-44 (English translation included).

Song-Gun Kim et al., "A Novel Denitrifying Bacterial Isolate that Degrades Trimethylamine Both Aerobically and Anaerobically via Different Pathways". Arch Microbiol., 2001, vol. 176, No. 4, 271-277.

Meiying Xu et al., "*Shewanella decolorationis* sp. Nov., a dye decolorizing bacterium isolated from activated sludge of a wastewater treatment plant". International Journal of Systematic and Evolutionary Microbiology, Jan. 2005, vol. 55, No. Pt 1, 363-8.

International Seach Report, PCT/JP2006/308416, mailed Jul. 11, 2006.

Rossetti S et al., "*Microthrix parvicella*, a filamentous bacterium causing bulking and foaming in activated sludge systems: a review of current knowledge", FEMS Microbiology reviews, 2005, pp. 49-64, vol. 29.

Hong Chua et al., "Effect of Food: Microorganism Ratio in Activated Sludge Foam Control", XP-002670562, 2000, pp. 1127-1135, vol. 84-86.

Harker A R et al., "Trichloroethylene Degradation by Two Independent Aromatic-Degrading Pathways in *Alcaligenes eutrophus* JMP134", XP-002670471, 1990, pp. 1179-1181, vol. 56, No. 4.

Das Subrata K et al., "Oxidation of Thiosulfate by a New Bacterium, *Bosea thiooxidans* (strain Bl-42) gen. nov., sp. nov.: Analysis of Phylogeny Based on Chemotaxonomy and 16S Ribosomal DNA Sequencing", XP-002670472, 1996, pp. 981-987, vol, 46, No. 4.

Extended European Search Report for corresponding EP Application No. 11188264.3-2406, Mar. 14, 2012.

Extended European Search Report for corresponding EP Application No. 11188252.8-2406, Mar. 14, 2012.

Chinese Office Action for corresponding CN Application No. 201110050797.2, May 17, 2013.

Taiwanese Office Action for corresponding TW Application No. 100120621, Aug. 13, 2013.

P. Kaempfer et al., "Characterization of Bacterial Communities From Activated Sludge: Culture-Dependent Numerical Identification Versus In Situ Identification Using Group- and Genus-Specific rRNA-Targeted Oligonucleotide Probes" Microbial Ecology, Springer-Verlag, New york, US, vol. 32, (Jan. 1, 1996), XP009007753, pp. 101-121.

Stefan Juretschko et el., "The Microbial Community Composition of a Nitrifying-Denitrifying Activated Sludge from an Industrial Sewage Treatment Plant Analyzed by the Full-Cycle rRNA Approach" Systematic and Applied Microbiology, vol. 25, (Jan. 1, 2002), pp. 84-99.

Zhang Chunlong et al., "Nutrient and surfactant enhancement for the biodegradation of chlorinated hydrocarbons in the wastewater from a Louisiana Superfund site", Journal of Hazardous Materials, Sep. 11, 1998, pp. 41-58, vol. 62, No. 1, XP002595255.

Clauss Fredric et al., "Controlling the settling of activated sludge in pulp and paper wastewater treatment plants", Water science and technology, Dec. 1999, pp. 223-229, vol. 40, No. 11-12, XP002595257.

Bidault A et al., "Floc agglomeration and structuration by a specific talc mineral composition", Water science and technology, Oct. 28, 1996, pp. 57-68, vol. 36, No. 4, XP002595256.

Lemmer H et al., "Scum in activated sludge plants: Impact of non-filamentous and filamentous bactertia", Acta hydochemica et hydrobiologica, Feb. 2000, pp. 34-40, vol. 28, No. 1, XP002595258.

Gao J et al., "Glucose-induced biodegradation of cis-dichloroethylene under aerobic conditions", Water research, Aug. 1, 1999, pp. 2789-2796, vol. 33, No. 12, XP004174046.

Takeno K et al., "Treatment of oil-containing sewage wastewater using immobilized photosynthetic bacteria", World journal of microbiology and biotechnology, Dec. 1, 2005, pp. 1385-1391, vol. 21, No. 8-9, XP019271706.

Extended European Search Report for corresponding EP Application No. 10155832.8-2406, Sep. 23, 2010.

* cited by examiner

SEQUENCE LISTING

```
<160> NUMBER OF SEQ ID NOS: 8

<210> SEQ ID NO 1
<211> LENGTH: 1532
<212> TYPE: DNA
<213> ORGANISM: Unknown
<220> FEATURE:
<223> OTHER INFORMATION: Alcaligenes

<400> SEQUENCE: 1
taaaggaggt gaccagccgc accttccgat acggctacct tgttacgact tcaccccagt      60
catgaatccc accgtggtaa gcgccccct tgcggttagg ctacctactt ctggtgaaac      120
ccactcccat ggtgtgacgg gcggtgtgta caagacccgg gaacgtattc accgcgacat     180
tctgatccgc gattactagc gattccgact tcacgcagtc gagttgcaga ctgcgatccg     240
gactacgatc gggtttctga gattggctcc ccctcgcggg ttggcgaccc tctgtcccga     300
ccattgtatg acgtgtgaag ccctacccat aagggccatg aggacttgac gtcatcccca     360
ccttcctccg gtttgtcacc ggcagtctca ttagagtgct cttgcgtagc aactaatgac     420
aagggttgcg ctcgttgcgg gacttaaccc aacatctcac gacacgagct gacgacagcc     480
atgcagcacc tgtgttccgg ttctcttgcg agcacggcca aatctcttcg gctttccaga     540
catgtcaagg gtaggtaagg tttttcgcgt tgcatcgaat taatccacat catccaccgc     600
ttgtgcgggt ccccgtcaat tcctttgagt tttaatcttg cgaccgtact ccccaggcgg     660
tcaacttcac gcgttagctg cgctactaag gcctaacggc cccaacagct agttgacatc     720
gtttagggcg tggactacca gggtatctaa tcctgtttgc tccccacgct ttcgtgtctg     780
agcgtcagta ttatcccagg gggctgcctt cgccatcggt attcctccac atatctacgc     840
atttcactgc tacacgtgga attctacccc cctctgacat actctagctc ggcagttaaa     900
aatgcagttc caaggttgag ccctgggatt tcacatcttt ctttccgaac cgcctacaca     960
cgctttacgc ccagtaattc cgattaacgc ttgcaccta cgtattaccg cggctgctgg    1020
cacgtagtta gccggtgctt attctgcaga taccgtcagc agtatctcgt attaggagat    1080
accttttctt ctctgccaaa agtactttac aacccgaagg ccttcatcat acacgcggga    1140
tggctggatc agggtttccc ccattgtcca aaattcccca ctgctgcctc ccgtaggagt    1200
ctgggccgtg tctcagtccc agtgtggctg gtcgtcctct caaaccagct acggatcgtt    1260
gccttggtga gcctttaccc caccaactag ctaatccgat atcggccgct ccaatagtga    1320
gaggtcttgc gatccccccc tttccccgt agggcgtatg cggtattagc cactctttcg    1380
agtagttatc ccccgctact gggcacgttc cgatatatta ctcacccgtc cgccactcgc    1440
cgccaagaga gcaagctctc tcgcgctgcc gttcgacttg catgtgtaaa gcatcccgct    1500
agcgttcaat ctgagccagg atcaaactct aa                                  1532
```

<210> SEQ ID NO 2
<211> LENGTH: 1498
<212> TYPE: DNA
<213> ORGANISM: Unknown
<220> FEATURE:
<223> OTHER INFORMATION: Sphingobacterium

<400> SEQUENCE: 2

| | | | | | | |
|---|---|---|---|---|---|---|
| ccagccgcac | cttccggtac | ggctaccttg | ttacgactta | gccccaatta | tcggttttac | 60 |
| cctaacacgc | tccttgcggt | tacatgcttt | aggcaccccc | aactttcatg | gcttgacggg | 120 |
| cggtgtgtac | aaggcccggg | aacgtattca | ccgcgtcatt | gctgatacgc | gattactagc | 180 |
| gaatccaact | tcatgaggtc | gagttgcaga | cctcaatccg | aactgtgaat | ggcttttcga | 240 |
| gattagcatc | ctgttaccag | gtagctgccc | gctgtaccat | ccattgtagc | acgtgtgtag | 300 |
| ccccggacgt | aagggccatg | atgacttgac | gtcgtcccca | ccttcctcac | agcttacgct | 360 |
| ggcagtctgt | ttagagtccc | catcattaca | tgctggcaac | taaacatagg | ggttgcgctc | 420 |
| gttgcgggac | ttaacccaac | acctcacggc | acgagctgac | gacagccatg | cagcacctag | 480 |
| tttcctgtcc | cgaaggactt | atctatctct | agataattca | gtaactttca | gcccgggta | 540 |
| aggttcctcg | cgtatcatcg | aattaaacca | catgctcctc | cgcttgtgcg | ggccccgtc | 600 |
| aattcctttg | agtttcaccc | ttgcgggcgt | actcccagg | tggataactt | aacgctttcg | 660 |
| ctaagacgct | gactgtgtat | cgccaacatc | gagttatcat | cgtttagggc | gtggactacc | 720 |
| agggtatcta | atcctgttcg | atccccacgc | tttcgtgcat | cagcgtcaat | aatgacttag | 780 |
| acagctgcct | tcgcaatcgg | agttctgaga | catatctatg | catttcaccg | ctacttgtct | 840 |
| cattccgcca | tcttcaacca | cattcaagct | catcagtatc | aaaggcactg | cgacagttga | 900 |
| gctgccgtct | ttcaccctg | acttaatgag | ccgcctacgc | acccttaaa | cccaataaat | 960 |
| ccggataacg | ctcggatcct | ccgtattacc | gcggctgctg | gcacggagtt | agccgatcct | 1020 |
| tattcttcca | gtacattcaa | gccactacac | gtagtggtgg | ttattcctgg | gacaaaagca | 1080 |
| gtttacaacc | catagggcag | tcatcctgca | cgcggcatgg | ctggttcaga | gttccctcca | 1140 |
| ttgaccaata | ttccttactg | ctgcctcccg | taggagtctg | gtccgtgtct | cagtaccagt | 1200 |
| gtggggatt | ctcctctcag | agcccctaga | catcgtagcc | ttggtaagcc | gttaccttac | 1260 |
| caactagcta | atgtcacgcg | agcccatcca | tatcctataa | atatttaaca | acatctcgat | 1320 |
| gccgagtcgt | tgtgtcatgc | ggtgttaatc | cggatttctc | cgggctatcc | ccctgatatg | 1380 |
| ggtaggttgc | tcacgcgtta | cgcacccgtg | cgccactctc | actaaatcta | agcaagctta | 1440 |
| gatctagatc | ccgtccgact | tgcatgtatt | aggcctgccg | ctagcgttca | tcctgagc | 1498 |

<210> SEQ ID NO 3
<211> LENGTH: 1513
<212> TYPE: DNA
<213> ORGANISM: Unknown
<220> FEATURE:
<223> OTHER INFORMATION: Shewanella algae

<400> SEQUENCE: 3

| | | | | | | |
|---|---|---|---|---|---|---|
| cagccccagg | ttcccctagg | gctaccttgt | atacgacttc | accccagtca | tgaaccacac | 60 |
| cgtggtaaac | gccctcccga | aggttaagct | atctactttct | ggtgcagccc | actcccatgg | 120 |
| tgtgacgggc | ggtgtgtaca | aggcccggga | acgtattcac | cgtggcattc | tgatccacga | 180 |
| ttactagcga | ttccgacttc | atggagtcga | gttgcagact | ccaatccgga | ctacgaccgg | 240 |
| ctttatgaga | ttagctccac | ctcgcggctt | cgcaaccctc | tgtaccgacc | attgtagcac | 300 |

```
gtgtgtagcc ctactcgtaa gggccatgat gacttgacgt cgtccccacc ttcctccggt      360
ttatcaccgg cagtctccct aaagttccg gcattacccg ctggcaagta aggatagggg       420
ttgcgctcgt tgcgggactt aacccaacat ttcacaacac gagctgacga cagccatgca      480
gcacctgtct cagagttccc gaaggcacca atccatctct ggaaagttct ctggatgtca      540
agagtaggta aggttcttcg cgttgcatcg aattaaacca catgctccac cgcttgtgcg      600
ggcccccgtc aattcatttg agttttaacc ttgcggccgt actccccagg cggtctactt      660
aatgcgttag cttgagagcc cagtgttcaa gacaccaaac tccgagtaga catcgtttac      720
ggcgtggact accagggtat ctaatcctgt ttgctcccca cgctttcgtg cctgagcgtc      780
agtctttgtc caggggccg ccttcgccac cggtattcct ccagatctct acgcatttca       840
ccgctacacc tggaattcta cccccctcta caagactcta gtttgccagt tcgaaatgcg      900
gttcccaggt tgagcccggg ctttcacat ctcgcttaac aaaccgcctg cgcacgcttt       960
acgcccagta attccgatta cgctcgcac cctccgtatt accgcggctg ctggcacgga      1020
gttagccggt gcttcttctg cgagtaacgt cacagatgta aggtattaac ttacacccctt    1080 tcctcctcgc tgaaagtgct ttacaacccg aaggccttct tcacacacgc ggcatggctg     1140
catcagggtt ccccccattg tgcaatattc cccactgctg cctcccgtag gagtctgggc     1200
cgtgtctcag tcccagtgtg gctgatcatc ctctcagacc agctagggat cgttgcctag    1260
gtgagccatt acctcaccta ctagctaatc ccacctgggc ttatccatca gcgcaaggac    1320
cgaaggtccc ctgctttccc ccgtagggcg tatgcggtat tagcagtcgt ttccaactgt    1380
tatcccccac aaatgggcaa attcccaggc attactcacc cgtccgccgc tcgtcatctt    1440
caaaagcaag cttttgaaat gttaccgctc gacttgcatg tgttaggcct gccgccagcg    1500
ttcaatctga gca                                                        1513

<210> SEQ ID NO 4
<211> LENGTH: 1448
<212> TYPE: DNA
<213> ORGANISM: Unknown
<220> FEATURE:
<223> OTHER INFORMATION: Rhodobacter

<400> SEQUENCE: 4
cagccgcagg ttcccctacg gctaccttgt tacgacttca ccccagtcgc tgaacccacc       60
gtggttggct gcctcctctt gcgaggttgg cgcaccacct tcgggtagat ccaactccca      120
tggtgtgacg ggcggtgtgt acaaggcccg ggaacgtatt caccgcgtca tgctgttacg      180
cgattactag cgattccgac ttcatggggt cgagttgcag accccaatcc gaactgagac      240
agctttttgg gattagccca ttgtcactgc cattgtagca cgtgtgtagc ccaacccgta      300
agggccatga ggacttgacg tcatccacac cttcctccga cttatcatcg gcagttctcc      360
tagagtgccc aactgaatgc tggcaactaa gagtgtgggt tgcgctcgtt gccggactta      420
accgaacatc tcacgacacg agctgacgac agccatgcag cacctgtgtg ggatccagcc      480
gaactgaaga aatccatctc tggaaatcgc gatccccatg tcaagggttg gtaaggttct      540
gcgcgttgct tcgaattaaa ccacatgctc caccgcttgt gcggccccc gtcaattcct      600 ttgagtttta atcttgcgac cgtactcccc aggcggaatg cttaatccgt taggtgtgtc     660
accgaattgc atgcaacccg acgactggca ttcatcgttt acggcgtgga ctaccagggt    720
atctaatcct gtttgctccc cacgctttcg cacctcagcg tcagtatcga ccagtgagc     780 cgccttcgcc actggtgttc ctccgaatat ctacgaattt cacctctaca ctcggaattc    840
```

```
cactcacctc tctcgaactc cagaccgata gttttgaagg cagttccggg gttgagcccc    900
gggatttcac ccccaacttt ccgatccgcc tacgtgcgct ttacgcccag taattccgaa    960
caacgctagc cccctccgta ttaccgcggc tgctggcacg gagttagccg ggcttcttc   1020 tgctggtacc gtcattatct tcccagctga aagagcttta caaccctaag gccttcatcg   1080
ctcacgcggc atggctagat cagggtttcc cccattgtct aagattcccc actgctgcct   1140
cccgtaggag tctgggccgt gtctcagtcc cagtgtggct gatcatcctc tcaaaccagc   1200
tatggatcgt cggcttggta ggccattacc ccaccaacta cctaatccaa cgcgggctaa   1260
tccttctccg ataaatcttt cccccgtagg gcgtatacgg tattactccc agtttcccga   1320
ggctattccg tagaaaaggg catattccca cgcgttactc acccgtccgc cgctaggacc   1380
gaagtcctcg ctcgactgca tgtgttaggc ctgccgccag cgttcgttct gagcaggatc   1440
aaactcta                                                            1448
```

<210> SEQ ID NO 5
<211> LENGTH: 1506
<212> TYPE: DNA
<213> ORGANISM: Unknown
<220> FEATURE:
<223> OTHER INFORMATION: Micrococcus luteus

<400> SEQUENCE: 5

```
taaaggaggt gatccagccg caccttccgg tacggctacc ttgttacgac ttagtcccaa     60
tcgctggtcc caccttcgac ggctcccccc acaagggtta ggccaccggc ttcgggtgtt    120
accaactttc gtgacttgac gggcggtgtg tacaaggccc gggaacgtat tcaccgcagc    180
gttgctgatc tgcgattact agcgactccg acttcatggg gtcgagttgc agaccccaat    240
ccgaactgag accggctttt tgggattagc tccacctcac agtatcgcaa cccattgtac    300
cggccattgt agcatgcgtg aagcccaaga cataaggggc atgatgattt gacgtcgtcc    360
tcaccttcct ccgagttgac cccggcagtc tcccatgagt ccccaccacg acgtgctggc    420
aacatggaac gagggttgcg ctcgttgcgg gacttaaccc aacatctcac gacacgagct    480
gacgacaacc atgcaccacc tgtgaacccg ccccaaaggg gaaaccgtat ctctacggcg    540
atcgagaaca tgtcaagcct tggtaaggtt cttcgcgttg catcgaatta atccgcatgc    600
tccgccgctt gtgcgggccc ccgtcaattc ctttgagttt tagccttgcg gccgtactcc    660
ccaggcgggg cacttaatgc gttagctgcg gcgcggaaac cgtggaatgg tccccacacc    720
tagtgcccaa cgtttacggc atggactacc agggtatcta atcctgttcg ctccccatgc    780
tttcgctcct cagcgtcagt tacagcccag agacctgcct tcgccatcgg tgttcctcct    840
gatatctgcg cattccaccg ctacaccagg aattccagtc tcccctactg cactctagtc    900
tgcccgtacc caccgcagat ccggggttaa gccccggact ttcacgacag acgcgacaaa    960
ccgcctacga gctctttacg cccaataatt ccggataacg ctcgcaccct acgtattacc   1020
gcggctgctg gcacgtagtt agccggtgct tcttctgcag gtaccgtcac tttcgcttct   1080
tccctactga aagaggttta caacccgaag gccgtcatcc ctcacgcggc gtcgctgcat   1140
caggcttgcg cccattgtgc aatattcccc actgctgcct cccgtaggag tctgggccgt   1200
gtctcagtcc cagtgtggcc ggtcaccctc tcaggccggc tacccgtcgt cgccttggtg   1260
agccattacc tcaccaacaa gctgataggc cgcgagtcca tccaaaaccg ataaatcttt   1320
ccaacaccca ccatgcggtg gacgctccta tccggtatta gacccagttt ccaggcttaa   1380
tcccagagtt aagggcaggt tactcacgtg ttactcaccc gttcgccact aatccaccca   1440
```

```
gcaagctggg cttcatcgtt cgacttgcat gtgttaagca cgccgccagc gttcatcctg    1500
agcagg                                                               1506

<210> SEQ ID NO 6
<211> LENGTH: 1422
<212> TYPE: DNA
<213> ORGANISM: Unknown
<220> FEATURE:
<223> OTHER INFORMATION: Paracoccus

<400> SEQUENCE: 6
ccagccgcag gttcccctac ggctaccttg ttacgacttc accccagtcg ctgagcctac     60
cgtggtccgc tgcccccatt gctggttagc gcacggccgt cgggtagacc caactcccat    120
ggtgtgacgg gcggtgtgta caaggcccgg gaacgtattc accgcggcat gctgttccgc    180
gattactagc gattccaact tcatgggggtc gagttgcaga ccccaatccg aactgagatg    240
gcttttgggg attaacccac tgtcaccacc attgtagcac gtgtgtagcc aacccgtaa     300 gggccatgag gacttgacgt catccacacc ttcctccgac ttatcatcgg cagttctctt    360
agagtgccca accaaatgct ggcaactaag agtgtgggtt cgctcgttg ccggacttaa     420 ccgaacatct cacgacacga gctgacgaca gccatgcagc acctgtctcc aggtcaccga    480
agtgaaagac ccgtctccgg gccggtcctg ggatgtcaag ggttggtaag gttctgcgcg    540
ttgcttcgaa ttaaaccaca tgctccaccg cttgtgcggg cccccgtcaa ttcctttgag    600
ttttaatctt gcgaccgtac tccccaggcg gaatgcttaa tccgttaggt gtgtcaccga    660
acagcatgct gcccgacgac tggcattcat cgtttacggc gtggactacc agggtatcta    720
atcctgtttg ctccccacgc tttcgcacct cagcgtcagt atcgagccag tgagccgcct    780
tcgccactgg tgttcctccg aatatctacg aatttcacct ctacactcgg aattccactc    840
acctctctcg aactccagac cgatagtttt gaaggcagtt ccggggttga gccccgggat    900
ttcaccccca actttccggt ccgcctacgt gcgctttacg cccagtaatt ccgaacaacg    960
ctagccccct ccgtattacc gcggctgctg gcacggagtt agccggggct tcttctgctg   1020
gtaccgtcat tatcttccca gctgaaagag ctttacaacc ctagggcctt catcactcac   1080
gcggcatggc tagatcaggg ttgccccat tgtctaagat tccccactgc tgcctcccgt    1140
aggagtctgg gccgtgtctc agtcccagtg tggctgatca tcctctcaaa ccagctatgg   1200
atcgtcggct tggtaggcca ttaccccacc aactacctaa tccaacgcgg gctaatcctt   1260
tggcgataaa tctttccccc gaagggcgca tacggtatta cccccagttt cccaggacta   1320
ttccgtacca aagggcatat cccacgcgt tactcacccg tccgccgctc accccgaagg    1380
gtgcgctcga cttgcatgtg taggcctgcc gccagcgttc gt                     1422

<210> SEQ ID NO 7
<211> LENGTH: 1448
<212> TYPE: DNA
<213> ORGANISM: Unknown
<220> FEATURE:
<223> OTHER INFORMATION: Bosea thiooxidans

<400> SEQUENCE: 7
cagccgcagg ttcccctacg gctaccttgt tacgacttca ccccagtcgc tgaccctacc     60
gtggtcgcct gcccccttgc ggttggcgca gcgccttcgg gtagaaccaa ctcccatggt    120
gtgacgggcg gtgtgtacaa ggcccgggaa cgtattcacc gcagcatgct gatctgcgat    180
tactagcgat tccgccttca tgcactcgag ttgcagagtg caatctgaac tgagacggct    240
```

-continued

```
tttggggatt agctccaggt cgcccttttcg ctgcccattg tcaccgccat tgtagcacgt    300
gtgtagccca gcccgtaagg gccatgagga cttgacgtca tccccacctt cctctcggct    360
tatcaccggc agtcccccta aagtgcccaa ctgaatgatg caactaggg gcgagggttg     420
cgctcgttgc gggacttaac ccaacatctc acgacacgag ctgacgacag ccatgcagca    480
cctgtgttct cgccagccga actgaaggaa accgtctccg gtatccaaac gagacatgtc    540
aagggctggt aaggttctgc gcgttgcttc gaattaaacc acatgctcca ccgcttgtgc    600
gggcccccgt caattccttt gagttttaat cttgcgaccg tactcccag gcgggatgct     660
taaagcgtta gctgcgccac tgagcagcaa gctgcccaac ggctagcatc catcgtttac    720
ggcgtggact accagggtat ctaatcctgt ttgctcccca cgctttcgcg cctcagcgtc    780
agatccggac cagtaagccg ccttcgccac tggtgttctt gcgaatatct acgaatttca    840
cctctacact cgcagttcca cttacctctt ccggtctcga cattccagt atcaaaggca    900
attccgaggt tgagccccgg gatttcaccc ctgacttaaa cgtccgccta cgcgcccttt    960
acgcccagtg attccgagca acgctagccc ccttcgtatt accgcggctg ctggcacgaa   1020
gttagccggg cttattcttc cggtaccgtc attatcgtcc cggataaaag agctttacaa   1080
ccctagggcc ttcatcactc acgcggcatg gctggatcag gcttgcgccc attgtccaat   1140
attccccact gctgcctccc gtaggagtct gggccgtgtc tcagtcccag tgtggctgat   1200
catcctctca gaccagctac tgatcgtcgc cttggtaggc cgttacccca ccaactagct   1260
aatcagacgc gggccgatcc ttcggcgata aatctttctc ctctcggacg tatccggtat   1320
tagctcaagt ttccctgagt tattccgaac caaagggcac gttcccacgc gttactcacc   1380
cgtctgccac tgtccccgaa ggaaccgttc gacttgcatg tgttaggcct gccgccagcg   1440
ttcgctct                                                             1448
```

<210> SEQ ID NO 8
<211> LENGTH: 1439
<212> TYPE: DNA
<213> ORGANISM: Unknown
<220> FEATURE:
<223> OTHER INFORMATION: Paracoccus verustus

<400> SEQUENCE: 8

```
taaaggaggt gaatccagcc gcaggttccc ctacggctac cttgttacga cttcacccca     60
gtcgctgagc ctaccgtggt ccgctgcctc ccgtgaaggg ttagcgcacg gccgtcgggt    120
agacccaact cccatggtgt gacgggcggt gtgtacaagg cccgggaacg tattcaccgc    180
ggcatgctgt tccgcgatta ctagcgattc caacttcatg ggtcgagtt gcagacccca    240
atccgaactg agatggcttt tgggattaa cccactgtca ccaccattgt agcacgtgtg    300
tagcccaacc cgtaagggcc atgaggactt gacgtcatcc acaccttcct ccgacttatc    360
atcggcagtt cttccagagt gcccaaccga atgatggcaa ctggaagtgt ggggttgcgct   420
cgttgccgga cttaaccgaa catctcacga cacgagctga cgacagccat gcagcacctg    480
tctccaggtc accgaagtga agacccgatc tctcgggctg tcctgggatg tcaagggttg    540
gtaaggttct gcgcgttgct tcgaattaaa ccacatgctc accgcttgt gcgggcccc     600
gtcaattcct ttgagttttta atcttgcgac cgtactcccc aggcggaatg cttaatccgt    660
taggtgtgtc accgaacagc atgctgcccg acgactggca ttcatcgttt acggcgtgga    720
ctaccagggt atctaatcct gtttgctccc cacgctttcg cacctcagcg tcagtatcga    780
gccagtgagc cgccttcgcc actggtgttc ctccgaatat ctacgaattt cacctctaca    840
```

-continued

```
ctcggaattc cactcacctc tctcgaactc cagaccgata gttttgaagg cagttccgag      900
gttgagcccc gggatttcac ccccaacttt ccggtccgcc tacgtgcgct ttacgcccag      960
taattccgaa caacgctagc cccctccgta ttaccgcggc tgctggcacg gagttagccg     1020
gggcttcttc tgctggtacc gtcattatct tcccagctga aagagcttta caaccctaag     1080
gccttcatca ctcacgcggc atggctagat cagggttgcc cccattgtct aagattcccc     1140
actgctgcct cccgtaggag tctgggccgt gtctcagtcc cagtgtggct gatcatcctc     1200
tcaaaccagc tatggatcgt cggcttggta ggccattacc ccaccaacta cctaatccaa     1260
cgcgggccga tcctttgccg ataaatcttt ccccgtagg gctcatgcgg tattactccc      1320
agtttcccag ggctattccg cagcaaaggg cacgttccca cgcgttactc acccgtccgc     1380
cgctagaacc gaagtcctcg ctcgacttgc atgtgttagg cctgccgcca gcgttcgtt     1439
```

METHOD OF TREATING WASTEWATER CONTAINING ORGANIC COMPOUND

This application is a national stage application of PCT/JP2006/308416, filed Apr. 21, 2006.

TECHNICAL FIELD

The present invention relates to a method of treating an organic substance-containing waste liquid and an apparatus for treating the organic substance-containing waste liquid, and a bacterium, a microbial culture, and an additive, each for treating an organic substance-containing waste liquid.

BACKGROUND ART

Waste liquids such as metal plating waste liquids and waste liquids from cleaning printed-circuit boards contain organic substances including, for example, higher alcohols, sulfide compounds, alkylthiosulfate compounds, nitrogen-containing alkyl compounds, phosphoric acid compounds, and the like in large amounts. Conventionally, the organic substance-containing waste liquid has been treated by, for example, subjecting an organic substance-containing waste liquid to steam-heating, thereby separating water as distilled water (see, for example, Japanese Patent Laid-Open No. 2003-89899); subjecting the organic substance-containing waste liquid to an electrolytic oxidation treatment or to a precipitation-and-collection treatment in the presence of chlorine ions (see, for example, Japanese Patent Laid-Open No. 2005-76103); subjecting the organic substance-containing waste liquid to frozen concentration to remove insoluble components (see, for example, Japanese Patent Laid-Open No. 2003-164862); or the like.

On the other hand, an organic substance-containing waste liquid such as a waste water from a food processing factory, a domestic waste water, or a raw sewage, has been treated according to an activated sludge method. However, when the activated sludge method is applied to the treatment of an organic substance-containing waste liquid such as a metal plating waste liquid or a waste liquid from cleaning a printed-circuit board, there are some disadvantages such as the removal of a substance affecting a BOD value or the like, the degradation removal of a sulfur-containing compound, and the removal ratios of a total nitrogen and a total phosphorus are low, so that the organic substance-containing waste liquid often produces foams or becomes turbid, thereby making it difficult to perform the treatment of the waste liquid. In addition, when the activated sludge method is applied to the treatment of an organic substance-containing waste liquid such as the metal plating waste liquid or the waste liquid from cleaning printed-circuit boards, there is a disadvantage that a foul odor may be generated in some cases.

In addition, scum is often generated in the process or equipment for treatment of a waste water, such as sewage treatment or domestic waste water treatment, and further experimental waste water treatment, factory waste water treatment, livestock waste water treatment, or sludge treatment, and is considered as a disadvantage as a great phenomenon of inhibiting normal operation of waste water of the process and equipment for treatment of a waste water. The scum is generated upon change of seasons (October to November and April to June in Japan), or when fluctuations of BOD loads are in extreme, i.e. when the load is light or excessive, or when BOD of a raw sewage is extremely high, or when a sludge concentration is extremely high, or upon fluctuations of pHs of a raw sewage, upon inflow of the sludge, upon lowering of a water temperature, or the like. In an earlier stage of generation of the scum, the sludge is suspended and separates from an aqueous phase to be suspended to cover the entire aeration tank, and the sludge flows into a precipitation tank and thus undesirably flows into a drainageway in the state of being incapable of providing liquid-solid separation. Also, since the liquid-solid separation can be prevented in the precipitation tank of the waste water treatment equipment, the quality of the treated water is drastically worsened. In addition, when the generated scum is allowed to stand, the activated sludge in the treatment tank forms scum, and the scum is in turn suspended, so that the contact of the foul water and the activated sludge is prevented, thereby impeding aeration efficiency, causing lowering of the treatment efficiency and causing treatment hindrance, and at the same time generating foul odor.

The above-mentioned generation of scum in an early state is also referred to as bulking, which is referred to those (1) in the state in which sedimentation of the sludge is controlled by the action of a filamentous fungus of the genus *Sphaerotilis*; (2) in the state in which bubbles that are less likely to be broken by aeration are formed (so-called foaming phenomenon), and sludge is adsorbed to the bubbles to be suspended, and the sludge is separated to form a layer on the surface of the aeration tank to be suspended (see *The Microbiology of Activated Sludge*, eds. R. J. Seviour et al., Kluwer Academic Publishers, Rordrecht, Netherlands, 1999, pp. 99-121, 147-202); and further (3) in the state where sludge is no longer suspended in water in the aeration tank, the sludge concentration tank or the precipitation tank even without the foaming phenomenon, so that the sludge is separated to be suspended; and the like.

In view of the above, the development of a method of controlling the generation of the scum, foaming or bulking, or eliminating the generated scum, foams or bulking in a very short period of time has been earnestly desired. For example, there is a method in which sedimentation property of the sludge is improved and the treatment efficiency of the activated sludge is improved, whereby consequently controlling the generation of scum (see Japanese Patent Laid-Open No. Hei 6-170387). When the scum is generated, the scum treatment is improved by adding alanine, magnesium sulfate, soluble silicic acid, or a silicate in a large amount against displacement to be treated; however, it has been reported that when a water temperature is elevated, the elimination of scum is not sufficient even with the treatment (Ryozo and Hideki (1999) *Journal of Antibacterial and Antifungal Agents, Japan*) 27(7): 431-440). As described in the same journal, a decisive solution strategy that can always be taken for the generation of scum, foaming or bulking against an operation at a low temperature, an operation at a high temperature, or an abnormal condition of treated water has not yet been found at present.

SUMMARY OF THE INVENTION

In one aspect, the present invention relates to the provision of a method of treating an organic substance-containing waste liquid, and a treatment apparatus therefor, and an additive for treating an organic substance-containing waste liquid, and a bacterium for degrading an organic substance component or the like in the waste liquid, each characterized by accomplishing at least one of treatment of the organic substance-containing waste liquid without substantially generating a foul odor, and obtainment of water quality that is suitable for releasing to sewage, a public water area, or the like. Also, in another aspect, the present invention relates to the provision of a microbial culture for treating an organic substance-containing waste liquid, characterized in that the microbial culture accomplishes the stable maintenance in the waste liquid containing organic substances, the degradation of organic substance components and the like in the waste liquid, and the like.

In another aspect, the present invention relates to the provision of a method of treating a degreasing agent-containing waste liquid, characterized by accomplishing at least one of treatment of the waste liquid without substantially generating a foul odor, and obtainment of water quality that is suitable for releasing to sewage, a public water area, or the like. In still another aspect, the present invention relates to the provision of a microbial culture for treating a degreasing agent-containing waste liquid, characterized in that the microbial culture accomplishes the stable maintenance in the waste liquid containing the degreasing agent, the degradation of degreasing agent components and the like in the waste liquid, and the like.

Even more, an object of the present invention is to develop a method of inexpensively and efficiently preventing and eliminating scum, foaming, and bulking even under all sorts of environments in waste water treatment equipments for sewage treatment, domestic waste water treatment, waste water treatment from biology laboratories, factory waste water treatment, livestock waste water treatment, sludge treatment and the like.

Specifically, as a means to solve the foregoing problems, the gist of the present invention relates to:

[1] a method of treating an organic substance-containing waste liquid, characterized in that the method comprises contacting:

an activated sludge containing one or more bacteria selected from the group consisting of bacteria belonging to the genus *Alcaligenes*, bacteria belonging to the genus *Sphingobacterium*, a bacterium of *Shewanella algae*, bacteria belonging to the genus *Rhodobacter*, a bacterium of *Micrococcus luteus*, bacteria belonging to the genus *Paracoccus*, a bacterium of *Bosea thiooxidans*, and a bacterium of *Paracoccus verustus*, and an organic substance-containing waste liquid;

[2] an apparatus for treating an organic-substance containing waste liquid used for the method as defined in the above [1], the apparatus comprising:

a treatment tank containing an activated sludge containing one or more bacteria selected from the group consisting of bacteria belonging to the genus *Alcaligenes*, bacteria belonging to the genus *Sphingobacterium*, a bacterium of *Shewanella algae*, bacteria belonging to the genus *Rhodobacter*, a bacterium of *Micrococcus luteus*, bacteria belonging to the genus *Paracoccus*, a bacterium of *Bosea thiooxidans*, and a bacterium of *Paracoccus verustus*; and a means of filtering a waste liquid in which an organic substance is degraded in the treatment tank with a submerged-membrane;

[3] an additive for treating an organic substance-containing waste liquid, comprising a magnesium compound, a silicon-containing compound and a nutritional supplement for cell culture;

[4] a method of treating a degreasing agent-containing waste liquid, characterized in that the method comprises contacting:

*Bosea thiooxidans*, *Paracoccus verustus* and a bacterium belonging to the genus *Paracoccus*, excluding *Paracoccus verustus*, and a degreasing agent-containing waste liquid;

[5] a microbial culture for treating a degreasing agent-containing waste liquid, comprising *Bosea thiooxidans*, *Paracoccus verustus*, and a bacterium belonging to *Paracoccus*, excluding *Paracoccus verustus*;

[6] a method of treating a degreasing agent-containing waste liquid, characterized in that the method comprises contacting:

a bacterium belonging to the genus *Alcaligenes*, a bacterium belonging to the genus *Sphingobacterium*, *Shewanella algae*, a bacterium belonging to the genus *Rhodobacter*, *Micrococcus luteus*, a bacterium belonging to the genus *Paracoccus*, and a degreasing agent-containing waste liquid;

[7] a microbial culture for treating a degreasing agent-containing waste liquid, comprising a bacterium belonging to the genus *Alcaligenes*, a bacterium belonging to the genus *Sphingobacterium*, *Shewanella algae*, a bacterium belonging to the genus *Rhodobacter*, *Micrococcus luteus*, and a bacterium belonging to the genus *Paracoccus*;

[8] a method of preventing or eliminating generation of scum, abnormal foaming and bulking in a step of treating waste water, characterized in that the method comprises adding a nutrient broth and/or alanine to a first vessel of an aeration tank in an amount of from 0.1 to 10 g/day per 1 cubic meter; and

[9] a bacterium having a characteristic of degrading an organic substance-containing waste liquid, wherein the bacterium is a bacterium selected from the group consisting of bacteria belonging to the genus *Alcaligenes*, bacteria belonging to the genus *Sphingobacterium*, a bacterium of *Shewanella algae*, bacteria belonging to the genus *Rhodobacter*, a bacterium of *Micrococcus luteus*, bacteria belonging to the genus *Paracoccus*, a bacterium of *Bosea thiooxidans*, and a bacterium of *Paracoccus verustus*.

According to the method of treating an organic substance-containing waste liquid and the apparatus for treating an organic substance-containing waste liquid, and a bacterium, a microbial culture, or an additive, each for treating an organic substance-containing waste liquid of the present invention, some excellent effects such as the organic substance-containing waste liquid can be treated with a high efficiency and a high treatment rate without substantially generating a foul odor, and at least water quality that is suitable for releasing to sewage, a public water area, or the like can be obtained are exhibited.

Also, according to the method of treating a degreasing agent-containing waste liquid of the present invention, some excellent effects such as the degreasing agent-containing waste liquid can be treated without substantially generating a foul odor, and water quality that is suitable for releasing to sewage, a public water area, or the like at least can be obtained are exhibited. In addition, according to the microbial culture for treating a degreasing agent-containing waste liquid of the present invention, some excellent effects that the microbial culture is stably maintained in the degreasing agent-containing waste liquid, and that a degreasing agent component or the like can be degraded are exhibited.

According to the present invention, generation of scum, generation of foams, and bulking are controlled, or can be very efficiently eliminated even under a drastic temperature change in a treatment liquid inside the waste water treatment equipment, especially an oxygen deficient state accompanying a low temperature of a water temperature of 10° C. or less in the wintry season, or a high temperature of 25° C. or more in the summer season, or a drastic change in pH or BOD. Further, the method of the present invention at the same time accomplishes the advantage of being able to easily carry out the method of the present invention with an inexpensive cost.

EXPLANATION OF NUMERICAL SYMBOLS

Figure 1:
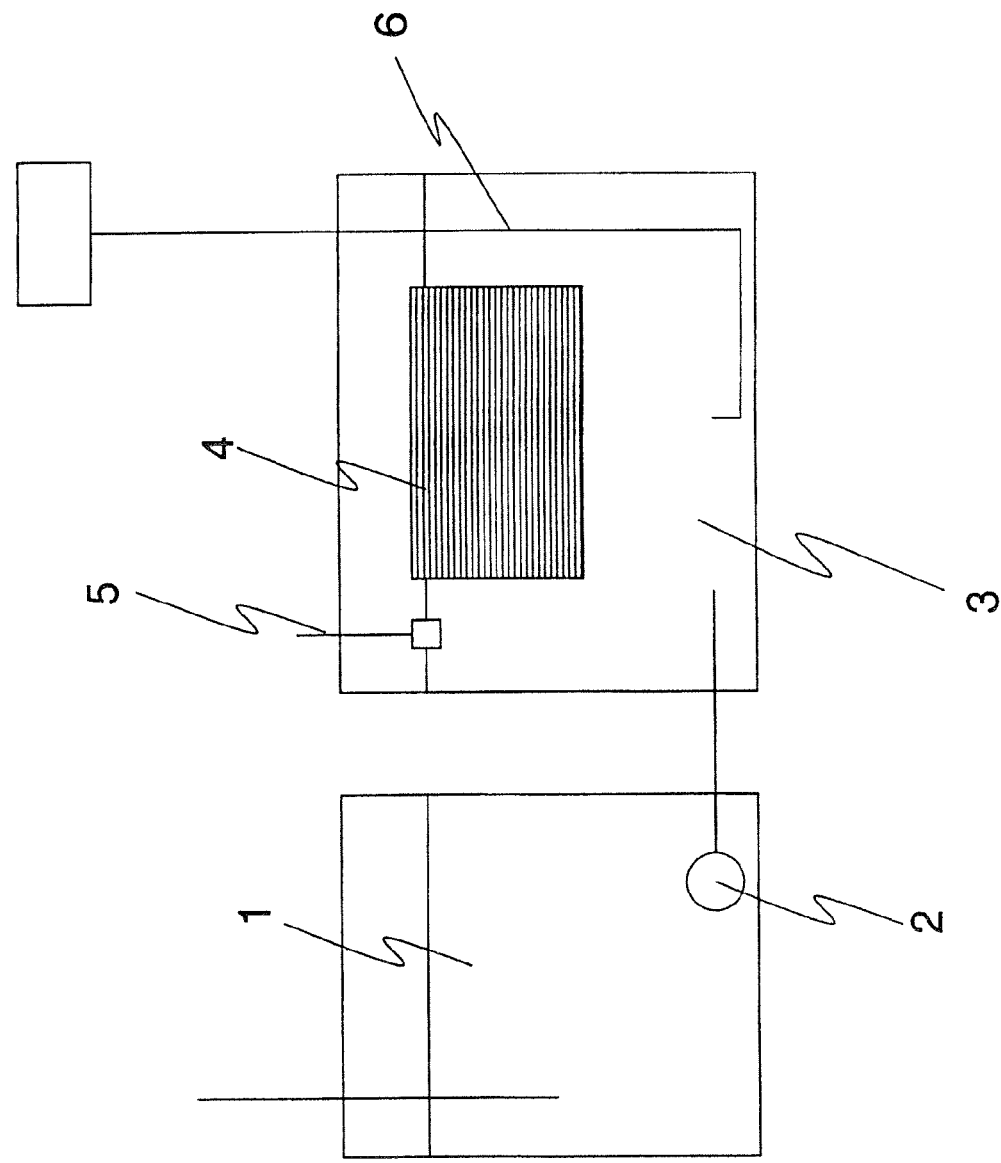
FIG. 1 is a schematic view of a plant for treating an organic substance-containing waste liquid.

1 Raw sewage tank
2 Submerged pump
3 Aeration tank
4 Hollow fiber membrane unit
5 Water level sensor
6 Diffuser pipe
21 Organism ante-relaying tank
22 First aeration tank of ante-aeration tank
23 Second aeration tank of ante-aeration tank
24 Third aeration tank of ante-aeration tank
25 Fourth aeration tank of ante-aeration tank
26 Precipitation tank
27 First aeration tank of post-aeration tank
28 Second aeration tank of post-aeration tank
29 Third aeration tank of ante-aeration tank
30 Submerged-membrane equipment

BEST MODE FOR CARRYING OUT THE INVENTION

In the method of treating an organic substance-containing waste liquid and the apparatus for treating an organic substance-containing waste liquid of the present invention, a specified bacterium, i.e. one or more bacteria selected from the group consisting of bacteria belonging to the genus *Alcaligenes*, bacteria belonging to the genus *Sphingobacterium*, a bacterium of *Shewanella algae*, bacteria belonging to the genus *Rhodobacter*, a bacterium of *Micrococcus luteus*, bacteria belonging to the genus *Paracoccus*, a bacterium of *Bosea thiooxidans*, and a bacterium of *Paracoccus verustus* (The term "bacterium" as referred to herein means these bacteria, unless specified otherwise) is used. Also, these bacteria used in the present invention are bacteria having a characteristic of degrading an organic substance-containing waste liquid.

The present invention relates to a method of treating an organic substance-containing waste liquid and an apparatus for treating an organic substance-containing waste water, characterized in that the method and the apparatus each comprises contacting an activated sludge in which the bacterium is present and the organic substance-containing waste liquid. In addition, the present invention may be a method of carrying out a waste liquid treatment using an additive for treating an organic substance-containing waste liquid and an apparatus therefor.

Here, the phrase "water quality that is suitable for releasing to sewage, a public water area, or the like" of the present invention may differ in standards depending on the local districts and the like in some cases. For example, the water quality includes water quality satisfying the conditions of standards for sewage release of Ogaki-shi, Gifu-ken, Japan on 2005 [pH: 5.0 to 9.0, BOD (River water release BOD+2× Mass of suspension): 600 mg/L or less, total nitrogen content: 240 mg/L or less, total phosphorus content: 32 mg/L or less], and the like.

In addition, the bacterium of the present invention exhibits an excellent characteristic that the bacterium is stably maintained even in an organic substance-containing waste liquid. Therefore, according to the present invention, an excellent effect that the organic substance-containing waste liquid can be stably treated without substantially being influenced by the organic substance components is exhibited.

Further, according to the present invention, the residence time in the aerating step upon contact with the activated sludge can be shortened, whereby an excellent effect that the organic substance-containing waste liquid can be treated in an even shorter time period is exhibited.

In addition, in the present invention, since the bacterium is used, the organic substance-containing waste liquid can be treated without substantially generating a foul odor.

In the present invention, the foul odor is evaluated by measuring hydrogen sulfide, ammonia, or the like using a detector manufactured by GASTEC CORPORATION (trade name: gas sampling kit GV-100S); measuring hydrogen sulfide gas, a combustible gas or the like using a detector manufactured by KOMYO RIKAGAKU KOGYO K.K. under the trade name of Multi-Gas Detector MD-701; and conducting a sensory test by randomly chosen plural individual, for example, one to five monitors; or the like.

In the method of treating an organic substance-containing waste liquid of the present invention, the culture of the bacterium alone, or a mixture of a plurality of cultures obtained separately, may be mixed with the organic substance-containing waste liquid, or the desired bacterium used in the present invention may be cultured the bacterium in an activated sludge.

In the method of treating an organic substance-containing waste liquid, the apparatus for treating an organic substance-containing waste liquid, and the additive for treating an organic substance-containing waste liquid of the present invention, the bacterium may be fluctuated depending upon the organic substance-containing waste liquid to be treated, and is not particularly limited. It is desired that the bacteria count is $1\times10^6$ CFU or more, more preferably $1\times10^7$ CFU or more, as determined by the dilution method per 1 mL of the organic substance-containing waste liquid, from the viewpoint of treating the organic substance-containing waste liquid efficiently, or that the bacteria count is up to a level of saturation amount. Here, the bacteria count is counted for a flat plate on which the colony forming unit to be counted is 30 to 300 CFU per one flat plate of the flat plates tested with a test water or a diluted test water at each stage, and the bacteria count is calculated by the following formula:

$$\text{The count of organisms per 1 ml of the sample} = \frac{(N1+N2+N3+\ldots Nn)}{n} \times \frac{1}{V} \times m \quad [\text{Su 1}]$$

wherein N1, N2, N3, . . . Nn each shows the colony forming unit (CFU); n is the number of flat plates; V is a volume (mL) of a test water or a diluted test water; m is a dilution fold of the test water.

Although the existing ratio of the bacteria (ratio of cell count) in the mixture or the activated sludge differs depending upon water quality of the inflow raw sewage, the retention time, the state of aeration, and the like, and it is desired that the existing ratio is of the same level.

The bacteria belonging to the genus *Alcaligenes* include *Alcaligenes faecalis*, and the like. More specifically, the bacteria include, for example, IBI-2P, and the like.

In addition, the nucleotide sequence of 16S rDNA of IBI-2P is the nucleotide sequence as shown in SEQ ID NO: 1.

Here, IBI-2P is named and identified as "IBI-2P," deposited to International Patent Organism Depositary, Independent Administrative Agency National Institute of Advanced Industrial Science and Technology (AIST Tsukuba Central 6, 1-1, Higashi 1-chome, Tsukuba-shi, Ibaraki-ken, Japan) under the accession number of FERM BP-10565 (date of deposit: Mar. 22, 2006 (original date of deposit: Apr. 27, 2005)).

The bacteria belonging to the genus *Sphingobacterium* include, more specifically, for example, IBI-3P, and the like. In addition, the nucleotide sequence of 16S rDNA of IBI-3P is the nucleotide sequence as shown in SEQ ID NO: 2. Here, IBI-3P is named and identified as "IBI-3P," deposited to International Patent Organism Depositary, Independent Administrative Agency National Institute of Advanced Industrial Science and Technology (AIST Tsukuba Central 6, 1-1, Higashi 1-chome, Tsukuba-shi, Ibaraki-ken, Japan) under the accession number of FERM BP-10566 (date of deposit: Mar. 22, 2006 (original date of deposit: Apr. 27, 2005)).

The bacterium of *Shewanella algae* includes, more specifically, for example, IBI-6P, and the like. In addition, the nucleotide sequence of 16S rDNA of IBI-6P is the nucleotide sequence as shown in SEQ ID NO: 3. Here, IBI-6P is named and identified as "IBI-6P," deposited to International Patent Organism Depositary, Independent Administrative Agency National Institute of Advanced Industrial Science and Technology (AIST Tsukuba Central 6, 1-1, Higashi 1-chome, Tsukuba-shi, Ibaraki-ken, Japan) under the accession number of FERM BP-10568 (date of deposit: Mar. 22, 2006 (original date of deposit: Apr. 27, 2005)).

The bacteria belonging to the genus *Rhodobacter* include, more specifically, for example, IBI-15P, and the like. In addition, the nucleotide sequence of 16S rDNA of IBI-15P is the nucleotide sequence as shown in SEQ ID NO: 4. Here, IBI-15P is named and identified as "IBI-15P," deposited to International Patent Organism Depositary, Independent Administrative Agency National Institute of Advanced Industrial Science and Technology (AIST Tsukuba Central 6, 1-1, Higashi 1-chome, Tsukuba-shi, Ibaraki-ken, Japan) under the accession number of FERM BP-10570 (date of deposit: Mar. 22, 2006 (original date of deposit: Apr. 27, 2005)).

The bacterium of *Micrococcus luteus* includes, more specifically, for example, IBI-40P, and the like. In addition, the nucleotide sequence of 16S rDNA of IBI-40P is the nucleotide sequence as shown in SEQ ID NO: 5. Here, IBI-40P is named and identified as "IBI-40P," deposited to International Patent Organism Depositary, Independent Administrative Agency National Institute of Advanced Industrial Science and Technology (AIST Tsukuba Central 6, 1-1, Higashi 1-chome, Tsukuba-shi, Ibaraki-ken, Japan) under the accession number of FERM BP-10571 (date of deposit: Mar. 22, 2006 (original date of deposit: Apr. 27, 2005)).

The bacteria belonging to the genus *Paracoccus* include, more specifically, for example, IBI-6, and the like. In addition, the nucleotide sequence of 16S rDNA of IBI-6 is the nucleotide sequence as shown in SEQ ID NO: 6. Here, IBI-6 is named and identified as "IBI-6," deposited to International Patent Organism Depositary, Independent Administrative Agency National Institute of Advanced Industrial Science and Technology (AIST Tsukuba Central 6, 1-1, Higashi 1-chome, Tsukuba-shi, Ibaraki-ken, Japan) under the accession number of FERM BP-10567 (date of deposit: Mar. 22, 2006 (original date of deposit: Apr. 27, 2005)).

The bacterium of *Bosea thiooxidans* includes, more specifically, for example, IBI-13, and the like. In addition, the nucleotide sequence of 16S rDNA of IBI-13 is the nucleotide sequence as shown in SEQ ID NO: 7. Here, IBI-13 is named and identified as "IBI-13," deposited to International Patent Organism Depositary, Independent Administrative Agency National Institute of Advanced Industrial Science and Technology (AIST Tsukuba Central 6, 1-1, Higashi 1-chome, Tsukuba-shi, Ibaraki-ken, Japan) under the accession number of FERM BP-10569 (date of deposit: Mar. 22, 2006 (original date of deposit: Apr. 27, 2005)).

The bacterium of *Paracoccus verustus* includes, more specifically, for example, IBI-2, and the like. In addition, the nucleotide sequence of 16S rDNA of IBI-2 is the nucleotide sequence as shown in SEQ ID NO: 8. Here, IBI-2 is named and identified as "IBI-2," deposited to International Patent Organism Depositary, Independent Administrative Agency National Institute of Advanced Industrial Science and Technology (AIST Tsukuba Central 6, 1-1, Higashi 1-chome, Tsukuba-shi, Ibaraki-ken, Japan) under the accession number of FERM BP-10564 (date of deposit: Mar. 22, 2006 (original date of deposit: Apr. 27, 2005)).

One embodiment of the present invention includes a method of treating an organic substance-containing waste liquid, characterized in that the method comprises contacting:

an activated sludge containing one or more bacteria selected from the group consisting of IBI-2P (Accession No.: FERM BP-10565), IBI-3P (Accession No.: FERM BP-10566), IBI-6P (Accession No.: FERM BP-10568), IBI-15P (Accession No.: FERM BP-10570), IBI-40P (Accession No.: FERM BP-10571), IBI-6 (Accession No.: FERM BP-10567), IBI-13 (Accession No.: FERM BP-10569), and IBI-2 (Accession No.: FERM BP-10564), and an organic substance-containing waste liquid.

In addition, another aspect of the method of treating an organic substance-containing waste liquid of the present invention includes adding an additive for treating an organic substance-containing waste liquid to an activated sludge containing the bacterium.

It is desired that each of the cultures of IBI-2P, IBI-2, IBI-3P, IBI-6P, IBI-15P, IBI-40P, IBI-6, and IBI-13, contains a carbon source in an amount of, for example, from 1 to 3% by weight, preferably from 1 to 1.6% by weight. In addition, it is desired that the culture contains a nitrogen source in an amount of, for example, from 0.5 to 2% by weight, preferably from 0.5 to 0.8% by weight. The culture is obtained by culturing the bacterium in a medium having a carbon source/nitrogen source ratio (C/N ratio) in the culture of from 40/1 to 3/1, preferably from 10/1 to 3/1, and especially preferably from 6/1 to 3.5/1, and a pH of from 7 to 8.9, preferably a pH of from 7 to 8 at 27° to 38° C., preferably at 30° C. for 3 to 7 days, preferably 4 to 5 days, at a rate of from 17 to 30 strokes/minute, and preferably from 20 to 25 strokes/minute. The medium includes, for example, a nutrient broth-glucose liquid medium containing a very small amount (0.01 to 0.05% by weight) of DMSO (composition: 0.8% by weight nutrient broth, 0.8% by weight glucose, 0.1% by weight dry yeast extract, pH 7), and the like.

The utilization of the organic substance-containing waste liquid by the bacterium is evaluated by, for example, measuring the biochemical oxygen demand (BOD), the chemical oxygen demand (COD), the total nitrogen content, and the total phosphorus content of the organic substance-containing waste liquid, and comparing the values before and after the treatment. Here, when each the BOD, the COD, the total nitrogen content, and the total phosphorus content of the water after the treatment is lowered as compared to each of the BOD, the COD, the total nitrogen content, and the total phosphorus content of the organic substance-containing waste liquid before the treatment, it serves as an index of utilizability of the bacterium for the organic substance-containing waste liquid.

The organic substance-containing waste liquid includes, for example, waste liquids discharged from plating factories, printed circuit board factories, and the like, printed board cleaning waste liquids, waste liquids pertaining to plating bath (catalyst giving, copper plating, nickel plating, gold plating), etching waste liquids, oxidation-reduction agent-containing waste liquids, waste liquids from food processing factories, domestic waste waters, raw sewage, and the like. Among them, the waste liquids discharged from plating factories, printed circuit board factories, and the like, the printed board cleaning waste liquids, the waste liquids pertaining to plating baths (catalyst giving, copper plating, nickel plating, gold plating), the etching waste liquids, the oxidation-reduction agent-containing waste liquids, and the like are also referred to herein as a degreasing agent-containing waste liquid.

In addition, the organic substance includes waste liquids pertaining to plating baths (catalyst giving, Cu plating, Au plating, etching waste liquids, the oxidation-reduction agent-containing waste liquids, and the like), printed board cleaning waste liquids (chemicals for cleaning, bath adjusting agents, and the like). Specifically, the organic substance includes, for example, a waste liquid containing at least one member selected from the group consisting of higher alcohols, sulfide compounds, higher alkyl sulfate compounds, alkyl thiosulfate compounds, nitrogen-containing alkyl compounds, phosphoric acid compounds, and the like. More specifically, the organic substance includes at least one member selected from the group consisting of diethylene glycol monobutyl ether, dipropylene glycol ether, monoethanolamine, polyoctyl phenyl ethers having an average molecular weight of from 696 to 872, isopropyl alcohol, ethylene glycol, N,N'-dimethylformamide, benzimidazoles having an alkyl group having 1 to 4 carbon atoms, alkyl sulfates having 20 to 22 carbon atoms, and the like.

One aspect of the method of treating an organic substance-containing waste liquid of the present invention includes a method characterized in that the method comprises subjecting an organic substance-containing waste liquid previously to the step of removing a metal, and thereafter contacting an organic substance in the organic substance-containing waste liquid in a treatment tank containing the activated sludge, to degrade the organic substance, or the method comprises after degrading the organic substance in the treatment tank, filtering the waste liquid with a submerged-membrane. The step of removing a metal is not particularly limited, and can be carried out by a conventional method. The step of removing a metal includes, for example, a lamellar separator, a Cu-chelating treatment, a Pb—Ag reducing treatment, a hydroxide treatment, a sulfide treatment, and the like.

The submerged-membrane used in the method of treating the waste liquid of the present invention is not particularly limited, and a hollow fiber membrane or a flat membrane is preferable.

In the method of the present invention, the treatment tank refers to a tank for degrading an organic substance in the organic substance-containing waste liquid, which, for example, refers to a tank in which an activated sludge containing the bacterium of the present invention, or an additive for treating an organic substance-containing waste liquid is used. Specifically, an aeration tank or the like is used as a treatment tank.

In the method of treating an organic substance-containing waste liquid of the present invention, the amount of dissolved oxygen (DO) is preferably 2 mg/L or more, and more preferably 3 mg/L or more, from the viewpoint of sufficiently exhibiting the utilization of the organic substance-containing waste liquid by the bacterium, and the amount of dissolved oxygen is preferably 8 mg/L or less, more preferably 7 mg/L or less, and even more preferably 6 mg/L or less, from the viewpoint of preventing the bulking and from the viewpoint of preventing abnormal foaming.

In the method of treating an organic substance-containing waste liquid of the present invention, it is desired that the raw waste water of the organic substance-containing waste liquid is adjusted to have a pH of preferably from 3.5 to 8.5, more preferably a pH of from 3.5 to 7.0, and even more preferably a pH of from 4.5 to 5.5, from the viewpoint of maintaining the pH in the aeration tank.

In the method of treating an organic substance-containing waste liquid of the present invention, it is desired that the pH of the waste water when the organic substance-containing waste liquid is contacted with the activated sludge, i.e. the pH of the waste water in the treatment tank which is a mixture of the activated sludge and the organic substance-containing waste liquid, is adjusted so that the pH is preferably from 6.0 to 9.0, the pH is more preferably from 6.5 to 9.0, the pH is even more preferably from 7.0 to 8.5, and the pH is still even more preferably from 7.5 to 8.0, from the viewpoint of sufficiently utilizing the organic substance-containing waste liquid by the bacterium. The pH of the organic substance-containing waste liquid is properly adjusted with, for example, a 25% by weight NaOH, a 18% by weight $H_2SO_4$, a 3% by weight HCl or the like.

In the method of treating an organic substance-containing waste liquid of the present invention, it is desired that the temperature of the mixture of the organic substance-containing waste liquid and the bacterium upon the contact therebetween is from 10° to 60° C., and preferably from 25° to 35° C., from the viewpoint of sufficiently utilizing the organic substance-containing waste liquid by the bacterium. Here, the temperature may be elevated with the progress of the treatment of the organic substance-containing waste liquid by the bacterium in some cases.

In the method of treating an organic substance-containing waste liquid of the present invention, the contact can be carried out in an appropriate treatment tank, for example, an aeration tank, or the like. Here, it is desired that the oxidation-reduction potential (ORP) in the treatment tank upon the contact is −100 mv or more, and preferably 0 mv or more, from the viewpoint of harmful influence of the reducing agent, and it is desired that the oxidation-reduction potential is 150 mv or less, and preferably 50 mv or less, from the viewpoint of harmful influence of the oxidation agent. The ORP is adjusted with, for example, an aqueous 5% by weight hydrogen peroxide.

In the aeration tank, when the activated sludge containing the bacterium is used, it is desired that the sludge weight index (SVI) after allowing the mixture of the organic substance-containing waste liquid and the activated sludge to stand for 30 minutes to sediment the activated sludge is within the range of from 50 to 150 or so, from the viewpoint of normal activated sludge management.

In the present invention, the additive for treating an organic substance-containing waste liquid is composed of a magnesium compound, a silicon-containing compound and a nutritional supplement for cell culture, and each of the magnesium compound, the silicon-containing compound and the nutritional supplement for cell culture is added to the treatment tank in the form of powder. Upon the addition, the magnesium compound, the silicon-containing compound and the nutritional supplement for cell culture may be added in a mixed state adjusted to a given ratio, or they may be separately added.

It is desired that the amount of the magnesium compound in the additive for treating an organic substance-containing waste liquid of the organic substance-containing waste liquid added to the treatment tank is from $2.0\times10^{-5}$ to $5.5\times10^{-3}$ mol/l, preferably from $8.0\times10^{-5}$ to $2.0\times10^{-3}$ mol/l, and more preferably from $2.0\times10^{-4}$ to $4.0\times10^{-3}$ mol/l, as expressed in an amount of mol of magnesium contained per 1 liter of the organic substance-containing waste liquid, from the viewpoint of sufficiently carrying out the utilization (degradation and removal) of the organic substance-containing waste liquid by the bacterium. The magnesium compound can be supplied by adding one or more members selected from, for example, magnesium sulfate, magnesium chloride, magnesium carbonate, and the like to the additive for treating an organic substance-containing waste liquid.

In addition, it is desired that the amount of the silicon-containing compound in the additive for treating an organic substance-containing waste liquid of the organic substance-containing waste liquid added to the treatment tank is from $3.0\times10^{-6}$ to $2.5\times10^{-3}$ mol/l, preferably from $3.0\times10^{-5}$ to $9.0\times10^{-3}$ mol/l, and more preferably from $1.5\times10^{-3}$ to $3.0\times10^{-3}$ mol/l, as expressed in an amount of mol of silicon contained per 1 liter of the organic substance-containing waste liquid, from the viewpoint of sufficiently carrying out utilization (degradation and removal) of the organic substance-containing waste liquid by the bacterium. The silicon-containing compound can be supplied by adding one or more members selected from, for example, diatomaceous earth, fly ash, cristobalite, volcanic rock, and obsidian, and the like to the additive for treating an organic substance-containing waste liquid.

In addition, it is desired that the amount of the nutritional supplement for cell culture in the additive for treating an organic substance-containing waste liquid of the organic substance-containing waste liquid added to the treatment tank is from 0.05 mg/L to 50 mg/L, preferably from 0.1 mg/L to 20 mg/L, and more preferably from 1 mg/L to 4 mg/L, as expressed in an amount of weight of the nutritional supplement for cell culture per 1 liter of the organic substance-containing waste liquid, from the viewpoint of sufficiently carrying out the utilization (degradation and removal) of the organic substance-containing waste liquid by the bacterium. In addition, the nutritional supplement for cell culture can be supplied by adding one or more members selected from, for example, nutrient broth, LB broth, and terrific broth, and the like to the additive for treating an organic substance-containing waste liquid. Alternatively, a gelatin hydrolysate, a beef extract or the like may be used.

In the present invention, it is desired in the additive for treating an organic substance-containing waste liquid that the mixing ratio of the magnesium compound to the silicon-containing compound (the number of moles of magnesium/the number of moles of silicon) is within the range of from $1.0\times10^{-2}$ to $1.6\times10^{3}$, and that the weight ratio of the nutritional supplement for cell culture to a total weight of the magnesium compound and the silicon-containing compound, (weight of the nutritional supplement for cell culture)/(weight of the magnesium compound+weight of the silicon-containing compound), is adjusted within the range of from $8.0\times10^{-5}$ to $2.0\times10^{1}$.

In the present invention, the additive for treating an organic substance-containing waste liquid is composed of a magnesium compound, a silicon-containing compound and a nutritional supplement for cell culture, each of which is adjusted within a ratio range, and in order to express the range of the ratio of the magnesium compound, the silicon-containing compound, and the nutritional supplement for cell culture, the ratio of the magnesium compound and the silicon-containing compound is expressed by the ratio of the number of moles of magnesium and silicon contained in each compound added. The ratio of the magnesium compound, the silicon-containing compound and the nutritional supplement for cell culture is expressed in a weight ratio of each compound added. The nutritional supplement for cell culture is composed of mainly amino acids. since the number of molecules are very large, the above expression method is adopted herein.

An apparatus for treating an organic substance-containing waste liquid using the method of treating an organic substance-containing waste liquid of the present invention is not particularly limited, and the apparatus may be an apparatus for treating an organic substance-containing waste liquid comprising a treatment tank containing an activated sludge containing the bacterium of the present invention; and a means of filtering a waste liquid in which an organic substance is degraded in the treatment tank with a submerged-membrane.

In the apparatus for treating an organic substance-containing waste liquid of the present invention, an amount of dissolved oxygen (DO), an additive for treating an organic substance-containing waste liquid, a pH of the raw waste water, a pH of a waste water in an aeration tank used as a treatment tank, a temperature, and an oxidation-reduction potential (ORP) may be the same as those mentioned above.

A still another embodiment of the present invention is a method of treating a degreasing agent-containing waste liquid, characterized in that the method comprises contacting a bacterium of *Bosea thiooxidans*, a bacterium of *Paracoccus verustus* and bacteria belonging to the genus *Paracoccus*, excluding *Paracoccus verustus*, and a degreasing agent-containing waste liquid.

Here, in this embodiment, the phrase "bacteria belonging to the genus *Paracoccus*" is intended to mean other bacteria belonging to the genus *Paracoccus* excluding *Paracoccus verustus*. Hereinafter, the bacteria may be expressed as "other bacteria belonging to the genus *Paracoccus*" in some cases.

In the method of treating a degreasing agent-containing waste liquid of the present invention, cultures obtained by separately culturing *Bosea thiooxidans*, *Paracoccus verustus* and other bacteria belonging to the genus *Paracoccus* may be mixed and used, or an activated sludge containing *Bosea thiooxidans*, *Paracoccus verustus* and other bacteria belonging to the genus *Paracoccus* may be used.

In the method of treating a degreasing agent-containing waste liquid of the present invention, the amount of dissolved oxygen (DO) is preferably 1 mg/L or more, more preferably 2 mg/L or more, and even more preferably 3 mg/L or more, and the amount of dissolved oxygen is preferably 8 mg/L or less, more preferably 7 mg/L or less, and even more preferably 6 mg/L or less, from the viewpoint of controlling bulking.

*Bosea thiooxidans*, *Paracoccus verustus* and the bacteria belonging to the genus *Paracoccus* include the bacteria as mentioned above.

As more specific examples, the present invention relates to a method of treating a degreasing agent-containing waste liquid, comprising contacting an activated sludge containing IBI-13 (FERM BP-10569), IBI-2 (FERM BP-10564), IBI-6 (FERM BP-10567), and a degreasing agent-containing waste liquid.

One aspect of the present invention includes a method of treating a degreasing agent-containing waste liquid, comprising contacting a microbial culture comprising IBI-13 (FERM BP-10569), IBI-2 (FERM BP-10564), and IBI-6 (FERM BP-10567), and a degreasing agent-containing waste liquid.

The degreasing agent-containing waste liquid, as mentioned above, includes, for example, waste liquids discharged from plating factories, printed circuit board factories, and the like, printed board cleaning waste liquids, waste liquids pertaining to plating bath (catalyst giving, Cu plating, Ni plating, Au plating), etching waste liquids, oxidation-reduction agent-containing waste liquids, and the like. In addition, the degreasing agent refers to chemicals for cleaning and bath adjusting agents. Specifically, the degreasing agent includes, for example, a waste liquid containing a higher alcohol, a sulfide compound, an alkyl thiosulfate compound, a nitrogen-containing alkyl compound, a phosphoric acid compound, and the like. More specifically, the degreasing agent includes diethylene glycol monobutyl ether, dipropylene glycol ether, monoethanolamine, polyoctyl phenyl ethers having an average molecular weight of from about 696 to about 872, isopropyl alcohol, ethylene glycol, N,N'-dimethylformamide, and benzimidazoles having an alkyl group having 1 to 4 carbon atoms [for example, a poly(2-alkylbenzimidazole-4,7 diyl)], and the like.

The degreasing agent-containing waste liquid includes, for example, a waste liquid containing at least one compound selected from the group consisting of diethylene glycol monobutyl ether, dipropylene glycol ether, monoethanolamine, polyoctyl phenyl ethers having an average molecular weight of from 696 to 872, isopropyl alcohol, ethylene glycol, N,N'-dimethylformamide, and benzimidazoles having an alkyl group having 1 to 4 carbon atoms, and the like.

It is desired that the pH of the degreasing agent-containing waste liquid at which *Bosea thiooxidans, Paracoccus verustus* and other bacteria belonging to the genus *Paracoccus*, and a degreasing agent-containing waste liquid are contacted is preferably adjusted so that the pH is preferably from 6.0 to 9.0, the pH is more preferably from 6.0 to 8.5, the pH is even more preferably from 6.5 to 8.0, and the pH is still even more preferably from 6.5 to 7.5, from the viewpoint of sufficiently utilizing the degreasing agent-containing waste liquid by the bacterium. The pH of the degreasing agent-containing waste liquid is properly adjusted with, for example, a 25% by weight NaOH, a 18% by weight $H_2SO_4$, a 3% by weight HCl or the like.

Upon the contact, *Bosea thiooxidans, Paracoccus verustus* and other bacteria belonging to the genus *Paracoccus*, and a degreasing agent-containing waste liquid can be contacted in an appropriate reaction tank, for example, an aeration tank, or the like. Here, upon the contact, it is desired that the oxidation-reduction potential (ORP) in the reaction tank is preferably −100 mv or more, more preferably −50 mv or more, and even more preferably 0 mv or more, and that the oxidation-reduction potential is preferably 150 mv or less, more preferably 100 mv or less, and even more preferably 50 mv or less, from the viewpoint of sufficiently growing *Bosea thiooxidans, Paracoccus verustus* and the other bacteria belonging to the genus *Paracoccus*. The ORP is adjusted with an aqueous hydrogen peroxide ($H_2O_2$), or the like.

In the reaction tank, when an activated sludge containing *Bosea thiooxidans, Paracoccus verustus* and other bacteria belonging to the genus *Paracoccus* is used, it is desired that the weight of the sludge after the mixture of the degreasing agent-containing waste liquid and the activated sludge is allowed to stand for 30 minutes to sediment the activated sludge is from 20 to 80%, from the viewpoint of facilitation of liquid-solid separation.

It is desired that the temperature at the contact is 35° C. or more, and preferably 38° C. or more, and that the temperature is 48° C. or less, and desirably 45° C. or less, from the viewpoint maintaining the active temperature of the microorganism.

It is desired that at the contact the pH of the mixture of *Bosea thiooxidans, Paracoccus verustus*, other bacteria belonging to the genus *Paracoccus*, and the degreasing agent-containing waste liquid is a pH of from 6.0 to 9.0, preferably a pH of from 6.4 to 8.7, and more preferably a pH of 7.5 to 8.7, from the viewpoint of sufficiently exhibiting the activity of the microorganism.

Here, the pH of the mixture can be adjusted, for example, in an aeration tank.

In another aspect, the present invention relates to a microbial culture for treating a degreasing agent-containing waste liquid, comprising *Bosea thiooxidans, Paracoccus verustus*, and a bacterium belonging to the genus *Paracoccus*.

Specifically, the microbial culture includes a mixture containing IBI-13, IBI-2, and IBI-6 mentioned above.

The carbon source in the culture includes, for example, meat extracts, glucose, peptone, and the like. In addition, the nitrogen source includes $NH_4Cl$, $(NH_4)_2SO_4$, meat extracts, peptone, and the like.

Here, the microbial culture of the present invention may be one in which *Bosea thiooxidans, Paracoccus verustus*, and a bacterium belonging to the genus *Paracoccus* are immobilized to a carrier made of a porous substance or the like. Alternatively, the microbial culture may be a mixture one in which *Bosea thiooxidans* is immobilized to the carrier, one in which *Paracoccus verustus* is immobilized to the carrier, and one in which the bacterium belonging to the genus *Paracoccus* is immobilized to the carrier.

Figure 2:
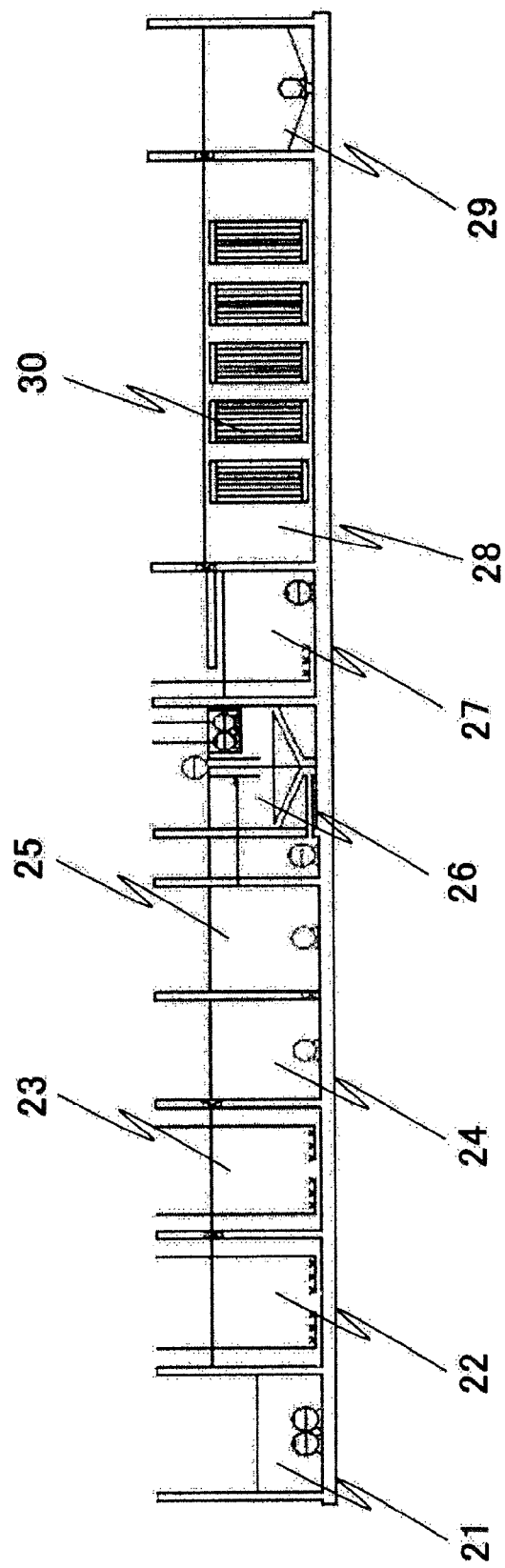
FIG. 2 is a schematic view of a treatment facility for treating an organic substance-containing waste liquid from plating factories or printed circuit board factories.

The method of treating a degreasing agent-containing waste liquid of the present invention can be carried out in, for example, a treatment facility for the degreasing agent-containing waste liquid, as shown in FIG. 2, or the like.

In a still another embodiment, the present invention relates to a method of treating a degreasing agent-containing waste liquid, characterized in that the method comprises contacting:

a bacterium belonging to the genus *Alcaligenes*, a bacterium belonging to the genus *Sphingobacterium, Shewanella algae*, a bacterium belonging to the genus *Rhodobacter, Micrococcus luteus*, and a bacterium belonging to the genus *Paracoccus*, and a degreasing agent-containing waste liquid.

In the method of treating a degreasing agent-containing waste liquid of the present invention, the amount of dissolved oxygen (DO) is preferably 2 mg/L or more, and more preferably 3 mg/L or more, from the viewpoint of sufficiently exhibiting the utilization of the degreasing agent-containing waste liquid by the bacterium, and the amount of dissolved oxygen is preferably 8 mg/L or less, more preferably 7 mg/L or less, and even more preferably 6 mg/L or less, from the viewpoint of preventing bulking and from the viewpoint of preventing abnormal foaming.

In the method of treating a degreasing agent-containing waste liquid of the present invention, the bacterium belonging to the genus *Alcaligenes*, the bacterium belonging to the genus *Sphingobacterium, Shewanella algae*, the bacterium belonging to the genus *Rhodobacter, Micrococcus luteus*, and the bacterium belonging to the genus *Paracoccus* may be used by mixing cultures obtained by separately culturing each bacterium, or may be used in the form of an active sludge containing the bacteria.

The existing ratio (ratio of cell count) of the bacterium belonging to the genus *Alcaligenes*, the bacterium belonging to the genus *Sphingobacterium, Shewanella algae*, the bacterium belonging to the genus *Rhodobacter, Micrococcus*

*luteus*, and the bacterium belonging to the genus *Paracoccus* in the mixture or the activated sludge may differ depending upon the water quality of inflow raw sewage, the residence time, the aeration state, and the like, and it is desired that the existing ratio is of the same level.

In addition, a more specific example of the present invention relates to a method of treating a degreasing agent-containing waste liquid comprising contacting an activated sludge containing IBI-2P, IBI-3P, IBI-6P, IBI-15P, IBI-40P, and IBI-6, and the degreasing agent-containing waste liquid.

The degreasing agent-containing waste liquid may be the same as that described in the above embodiment.

It is desired that the degreasing agent-containing waste liquid before the bacterium and the degreasing agent-containing waste liquid are contacted is adjusted so that the pH is preferably from 3.5 to 8.0, the pH is more preferably of from 3.5 to 7.0, and the pH is even more preferably from 4.5 to 5.5, from the viewpoint of maintaining the pH in the aeration tank.

When the bacterium and the degreasing agent-containing waste liquid are contacted, it is desired that the pH of the mixture of the bacterium and the degreasing agent-containing waste liquid is adjusted so that the pH is preferably from 6.0 to 9.0, the pH is more preferably from 6.5 to 9.0, the pH is even more preferably from 7.0 to 8.5, and the pH is still even more preferably from 7.5 to 8.0, from the viewpoint of sufficiently utilizing the degreasing agent-containing waste liquid by the bacterium. The pH of the degreasing agent-containing waste liquid is properly adjusted with, for example, a 25% by weight NaOH, a 18% by weight $H_2SO_4$, a 3% by weight HCl or the like.

Upon the contact, it is desired that the temperature of the mixture of the degreasing agent-containing waste liquid and the bacterium is from 15° to 40° C., and preferably from 25° to 35° C., from the viewpoint of sufficiently utilizing the degreasing agent-containing waste liquid by the bacterium. Here, the temperature may be raised with the progress of the treatment of the degreasing agent-containing waste liquid by the bacterium in some cases.

The contact can be carried out in an appropriate reaction tank, for example an aeration tank or the like. Here, upon the contact, it is desired that the oxidation-reduction potential (ORP) in the reaction tank is −100 mv or more, and preferably 0 mv or more, from the viewpoint of causing harmful influence of the reducing agent, and it is desired that the oxidation-reduction potential is 150 mv or less, and preferably 50 mv or less, from the viewpoint of causing harmful influence of the oxidizing agent. The ORP is adjusted with, for example, a 5% by weight aqueous hydrogen peroxide.

In the aeration tank, when the activated sludge containing the bacterium is used, it is desired that the sludge weight index (SVI) after the mixture of the degreasing agent-containing waste liquid and the activated sludge is allowed to stand for 30 minutes to sediment the activated sludge is within the range of 50 to 150 or so, from the viewpoint of normal activated sludge management.

It is preferable in the method of treating a degreasing agent-containing waste liquid of the present invention that magnesium ions are present in the mixture, from the viewpoint of sufficiently utilizing the degreasing agent-containing waste liquid by the bacterium. It is desired that the amount of the magnesium ions in the mixture is 0.5 mg/L (per tank) or more, and preferably 2 mg/L (per tank) or more, calculated as the content of the anhydrous magnesium sulfate, from the viewpoint of accelerating the treatment efficiency and maintaining the bacterial phase, and that the amount of the magnesium ions is preferably 500 mg/L (per tank) or less, more preferably 100 mg/L (per tank) or less, and even more preferably 50 mg/L or less, from the viewpoint of saving treatment costs. The magnesium ions can be supplied by adding, for example, magnesium sulfate, magnesium chloride, magnesium acetate or the like to the mixture.

In addition, it is preferable in the method of treating a degreasing agent-containing waste liquid of the present invention that silicic acid is present in the mixture, from the viewpoint of sufficiently utilizing the degreasing agent-containing waste liquid by the bacterium. It is desired that the amount of silicic acid in the mixture is 0.1 mg/L (per tank) or more, and preferably 1 mg/L (per tank) or more, calculated as the content of silicon, from the viewpoint of accelerating the treatment efficiency and maintaining the bacterial phase, and that the amount of the silicic acid is preferably 100 mg/L (per tank) or less, more preferably 70 mg/L (per tank) or less, and even more preferably 30 mg/L (per tank) or less, from the viewpoint of saving treatment costs.

In addition, it is preferable in the method of treating a degreasing agent-containing waste liquid of the present invention that a medium for growing a bacterium, such as nutrient broth, is present in the mixture, from the viewpoint of sufficiently utilizing the degreasing agent-containing waste liquid by the bacterium. For example, when the nutrient broth is used, it is desired that the content of the nutrient broth in the mixture is 0.05 mg/L (per tank) or more, and preferably 0.1 mg/L (per tank) or more, from the viewpoint of accelerating the treatment efficiency and maintaining the bacterial phase, and that the content of the nutrient broth in the mixture is 50 mg/L (per tank) or less, and preferably 20 mg/L (per tank) or less, from the viewpoint of saving treatment costs. In addition, a gelatin hydrolysate, a beef extract or the like may be used in place of the nutrient broth.

In another aspect, the present invention relates to a microbial culture for treating a degreasing agent-containing waste liquid, comprising a bacterium belonging to the genus *Alcaligenes*, a bacterium belonging to the genus *Sphingobacterium*, *Shewanella algae*, a bacterium belonging to the genus *Rhodobacter*, *Micrococcus luteus*, and a bacterium belonging to the genus *Paracoccus*.

A specific example of the microbial culture for treating a degreasing agent-containing waste liquid of the present invention include a mixture containing IBI-2P, IBI-3P, IBI-6P, IBI-15P, IBI-40P, and IBI-6.

The carbon source in the culture includes glucose, meat extract, peptone, and the like. The nitrogen source includes $NH_4Cl$, $(NH_4)_2SO_4$, meat extracts, peptone, and the like.

The microbial culture of the present invention may be obtained by immobilizing the bacteria to a carrier or the like, made of a porous substance or the like. In addition, the microbial culture may be a mixture of those obtained by immobilizing each of the bacteria to a separate carrier.

The present invention may be a method of treating a degreasing agent-containing waste liquid, comprising contacting a bacterium belonging to the genus *Alcaligenes*, a bacterium belonging to the genus *Sphingobacterium*, *Shewanella algae*, a bacterium belonging to the genus *Rhodobacter*, *Micrococcus luteus*, and a bacterium belonging to the genus *Paracoccus*, and a degreasing agent-containing waste liquid, in the presence of magnesium ions 0.5 to 500 mg/L (amount calculated as anhydrous magnesium sulfate), silicic acid 0.1 to 100 mg/L (amount calculated as silicon), and a nutrient broth 0.05 to 50 mg/L.

The method of treating a degreasing agent-containing waste liquid of the present invention may further comprise magnesium ions 0.5 to 500 mg/L (amount calculated as anhydrous magnesium sulfate), silicic acid 0.1 to 100 mg/L (amount calculated as silicon), and a nutrient broth 0.05 to 50 mg/L, and use the microbial culture comprising a bacterium belonging to the genus *Alcaligenes*, a bacterium belonging to the genus *Sphingobacterium*, a bacterium of *Shewanella algae*, a bacterium belonging to the genus *Rhodobacter*, a bacterium of *Micrococcus luteus*, and a bacterium belonging to the genus *Paracoccus*.

The method of treating a degreasing agent-containing waste liquid of the present invention may further comprise magnesium ions 0.5 to 500 mg/L (amount calculated as anhydrous magnesium sulfate), silicic acid 0.1 to 100 mg/L (amount calculated as silicon), and a nutrient broth 0.05 to 50 mg/L, and use a microbial culture comprising IBI-2P, IBI-3P, IBI-6P, IBI-15P, IBI-40P, and IBI-6.

The method of treating a degreasing agent-containing waste liquid of the present invention can be carried out, for example, in a treatment plant as shown in FIG. 1, or the like.

The nutrient broth usable in the present invention refers to a mixture of a partial hydrolysate of gelatin and a beef extract in a ratio of about 5:3 (weight ratio), and is commercially available under this name as a general bacterial medium. The amount of alanine added in a first tank of the aeration tank is from 0.1 to 10 g/day, and more preferably from 2 to 5 g/day, per 1 cubic meter of the first tank of the aeration tank (waste water to be treated).

Also, the alanine used in the present invention may be in the L-form, or the DL-form. In the case of the DL-form, the alanine becomes naturally racemic with the consumption of the L-form, and consumed in the L-form. Therefore, regardless of being the L-form or the DL-form, the amount of alanine added in a first tank of the aeration tank is from 0.1 to 10 g/day, per 1 cubic meter of the first tank of the aeration tank (waste water to be treated). In addition, the silicate used includes volcanic rock, obsidian, and magnesium silicate each in the form of fine powder.

One aspect of the present invention may be a method of preventing or eliminating generation of scum, abnormal foaming and bulking in a step of treating waste water, characterized in that the method comprises adding a nutrient broth and/or alanine to a first tank of an aeration tank in an amount of from 0.1 to 10 g/day per 1 cubic meter; or a method of preventing or eliminating generation of scum, abnormal foaming and bulking in a step of treating waste water, characterized in that the method comprises adding a silicate to an aeration tank (waste water to be treated) in an amount of from 1 to 10 g/day per 1 cubic meter.

INDUSTRIAL APPLICABILITY

According to the present invention, an organic substance-containing waste liquid discharged from plating factories, printed circuit board factories, or food processing factories, and an organic substance-containing waste liquid such as a domestic waste water or a raw sewage can be treated with high efficiency in a short period of time.

The present invention will be specifically described hereinbelow by the Examples, without intending to limit the scope of the present invention thereto.

EXAMPLE 1

A degreasing agent-containing waste liquid discharged from plating factories and printed factories was treated using an activated sludge as follows.

Here, the degreasing agent-containing waste liquid contained at least dipropylene glycol ether, an alkylbenzimidazole, a benzimidazole derivative, diethylene glycol monobutyl ether, monoethanolamine, a polyoctyl phenyl ether, isopropyl alcohol, ethylene glycol, N,N'-dimethylformamide, or the like.

In addition, the biochemical oxygen demand (BOD), the chemical oxygen demand (COD), the total nitrogen content, and the total phosphorus content were respectively determined for the degreasing agent-containing waste liquid. The BOD was obtained by measuring an amount of dissolved oxygen in a sample after 5 days of culture and an amount of dissolved oxygen in a sample before the culture using a product under the trade name of DO meter OM 12 (manufactured by HORIBA, Ltd.), and calculating the BOD on the bases of the numerical values of the amounts of dissolved oxygen obtained before and after the culture. The COD was evaluated by measuring an amount of oxygen chemically consumed using potassium permanganate. The total nitrogen content was evaluated by adding sodium hydroxide and potassium peroxodisulfate to the degreasing agent-containing waste liquid, heating the resulting mixture at 120° C. for 30 minutes, and adding hydrochloric acid to product obtained, and determining the absorbance of the resulting product at 220 nm in accordance with the ultraviolet absorbance photometry. The total phosphorus content was evaluated in accordance with nitric acid-sulfuric acid degradation method by adding nitric acid to the degreasing agent-containing waste liquid, heating the mixture to concentrate, thereafter adding nitric acid and sulfuric acid to a product obtained, heating the mixture to convert a phosphorus-containing compound to a phosphate ion, and to concurrently degrade an organic substance, and determining phosphate ions in the resulting product with molybdenum blue (reduced with ascorbic acid) absorbance photometry.

As a result, the degreasing agent-containing waste liquid had a BOD of about 4,300 ppm, and a COD of about 3,011 ppm. In addition, the degreasing agent-containing waste liquid had a total nitrogen content of about 619 ppm, and a total phosphorus content of about 225 ppm.

The degreasing agent-containing waste liquid was treated with a treatment plant as shown in FIG. 1. The numerals of each part hereinafter are based on FIG. 1. Specifically, the degreasing agent-containing waste liquid was successively transported to a raw sewage tank 1 made of a 500 L tank with a submerged pump 2 (manufactured by EBARA CORPORATION, under the trade name of Submerged Pump DWV6.15S). Here, in the raw sewage tank 1, 350 L of the degreasing agent-containing waste liquid was stored. In addition, in the raw sewage tank 1, a 25% by weight sodium hydroxide or a 18% by weight sulfuric acid was added to the degreasing agent-containing waste liquid, while measuring its pH with a pH meter (B-21) manufactured by HORIBA, Ltd., to thereby adjust its pH to 4.6 to 5.3.

The degreasing agent-containing waste liquid was transported to an aeration tank 3 (500×450×1600 mm, effective volume: 340 L) into which 340 L of an activated sludge was introduced from the raw sewage tank 1 with the submerged pump 2. Here, the waste water was transported from the raw sewage tank 1 to the aeration tank 3 so that the residence time of the degreasing agent-containing waste liquid in the aeration tank 3 was 42 hours using a water level sensor 5 (electrode pole) provided in the aeration tank 3.

The aeration tank 3 comprises a hollow fiber membrane unit 4 composed of 10 pieces of hollow fiber membranes (1 $m^2$, manufactured by Toray Industries, Ltd., under the trade name of SUR134) for filtering a liquid to be treated, and a diffuser pipe 6 for aerating the air. The hollow fiber membrane unit 4 is positioned in the center of the aeration tank 3 immediately above the diffuser pipe in the aeration tank 3, wherein the positioning of the unit 4 is such that the unit 4 can sufficiently receive the aeration of the air from the diffuser pipe 6. The diffuser pipe 6 can be positioned at a lower part of the aeration tank 3, so that an entire aeration tank 3 can be stirred with an air aeration. In the aeration tank 3, the aeration is carried out so that the air that is supplied from the diffuser pipe 6 passes through the hollow fiber unit 4 and descends along a wall surface of the aeration tank 3, while the activated sludge similarly is convected.

Further, in the aeration tank 3, diatomaceous earth, magnesium sulfate, and nutrient broth [manufactured by KYOKUTO PHARMACEUTICAL INDUSTRIAL CO., LTD, partial hydrolysate of gelatin 5: contained as a meat extract 3] were sequentially added to the mixture of the activated sludge and the degreasing agent-containing waste liquid, so that silicic acid was 5 mg/L per day, calculated as silicon content, magnesium sulfate was 10 mg/L per day, calculated as magnesium ions, and nutrient broth was 4.0 mg/L per day. In addition, the temperature of the mixture of the activated sludge and the degreasing agent-containing waste liquid in the aeration tank 3 was maintained at a temperature of from 10° to 17° C. The amount of air supplied to the aeration tank 3 was adjusted to 80 L/minute, whereby the amount of dissolved oxygen (DO) in the mixture was maintained at a level of from 2 to 7 mg/L. Further, the oxidation-reduction potential of the mixture was set to 50 mv.

Thereafter, the BOD, the COD, the total nitrogen content, and the total phosphorus content of the treated water that passed the aeration tank 3 were determined in the same manner as above.

As a result, the BOD was 124 ppm, the COD was 222 ppm, the total nitrogen content was 69 ppm, and the total phosphorus content was 10.8 ppm. The decreasing ratios of the BOD and the COD of the treated water to the BOD and the COD of the degreasing agent-containing waste liquid before the treatment were 97.1% and 92.6%, respectively, and the removal ratios of nitrogen and phosphorus were 88.9% and 95.2%, respectively.

Next, the activated sludge was stepwise diluted with sterile physiological saline. Each of the dilutions obtained was spread on a nutrient broth-glucose agar medium [0.8% by weight NUTRIENT BROTH (trade name) (manufactured by Oxoid, CM-1), 0.8% by weight glucose, 0.6% by weight sodium chloride, 0.1% by weight a dry yeast extract [manufactured by Difco], 1.5% by weight agar (manufactured by INA FOOD INDUSTRY Co., Ltd., under the trade name of BA-10), pH 7.0], and the dilution was cultured at 30° C. until colonies appeared. Thereafter, colonies of a microorganism were collected from the appearing colonies using the morphology and the color of the colonies as indices. The collected microorganism was spread on Columbia agar base (trade name), and cultured at 30° C. for 3 days. The collection and the culture of the microorganism were repeated until the morphology and the color of the colonies became even.

Next, in accordance with an ordinary method (for example, a method described in "*Biseibutsuno Bunruito Dotei Ge* (*Classification and Identification of Microorganisms, Volume Two*)," edited by Takeharu HASEGAWA, Gakkai Shuppan Senta, and Sakazaki, Yoshizaki et al. "Shinsaikinbaichigaku Koza Ge-1 (New Studies on Bacterial Medium Lecture Volume Two-1)," Kindai Shuppan or the like), gram staining, oxidase test, and other physiological and biochemical properties for each of the microorganisms were examined. In addition, the morphology and the motility of each of the microorganisms were observed using an optical microscope (attached with Labophoto phase-contrast device (trade name), manufactured by Nihon Kogaku (Nikon Corporation)). Further, a DNA was extracted from each of the microorganisms, and PCR was carried out using a thermal cycler (manufactured by ABI, 2730) with the DNA obtained as a template. The thermal profile of PCR was the conditions of incubating at 94° C. for 1 minute; carrying out 30 cycles of reaction, wherein one cycle consists of 94° C. for 1 minute, 63° C. for 1 minute, and 72° C. for 1.5 minutes; incubating at 72° C. for 2 minutes; and thereafter at 4° C. The resulting product was mixed with a PEG (Poly Ethylene Glycol: manufactured by Wako Pure Chemical Industries, Ltd.)/NaCl solution (30% (W/V)), and the mixture obtained was allowed to stand at 4° C. for 30 minutes to 1 hour. Thereafter, the mixture obtained was centrifuged at 11,000×g (14,000 rpm) for 10 minutes at room temperature, and the supernatant was removed. One milliliter of a 70% by weight chilled ethanol was added to the resulting product, and the mixture was centrifuged at 11,000×g (14,000 rpm) for 1 minute, the supernatant was discarded, and the residue was dried for 5 minutes. Twenty microliters of sterile purified water was added to the resulting product. The nucleotide sequence of the resulting product was determined using a kit manufactured by ABI under the trade name of BIGDYE® Terminator V 3.1 Cycle Sequencing Kit. The determined nucleotide sequence was analyzed for homology with the data of the nucleotide sequences in the DDBJ and NCBI Data Base. In the analysis based on the Data Base, the setting conditions for the parameters in the Blast search (Fasta) program are default conditions, i.e. Word Size: 11, Cost to open a gap: 0, Cost to extend a gap: 0, X dropoff value for gapped alignment 30, Penalty for a nucleotide mismatch: −3, Reward for a nucleotide match: 1, Threshold for extending hits: 0. In addition, the phylogenic analysis was carried out by calculating alignment on the basis of Clustal X 1.83, and preparing a phylogenic tree with Tree View. The setting conditions of the parameters in the Clustal X were Pairwise parameter (Gap opening 8-12, Gap extension 0.1-0.2), Multialignment parameter (Gap opening 8-12, Delay divergent sequence 15-30%, DNA transition weight 0.2-0.5). Here, when the determined nucleotide sequence had a homology with a nucleotide sequence in the Data Base of 99% or more, it is considered that the microorganism is a microorganism that is identical on a species level to the microorganism serving as an origin of the nucleotide sequence in the Data Base. Further, a phylogenic analysis was carried out and comprehensively judged. In addition, when the determined nucleotide sequence has a homology of 95% or more, the microorganism is a microorganism that is identical on a genus level to the microorganism serving as an origin of the nucleotide sequence in the Data Base. Further, a phylogenic analysis was carried out and comprehensively judged.

As a result, six kinds of bacteria, i.e. IBI-2P, IBI-3P, IBI-6P, IBI-15P, IBI-40P, and IBI-6 were isolated.

IBI-2P mentioned above was a gram-negative, aerobic bacterium, which was a *bacillus* having a size of 0.2×0.5 μm. When IBI-2P mentioned above was cultured on Columbia agar base (trade name) (manufactured by BBL, manufactured article number: 211124) at 30° C. for 3 days, colonies of a size having a diameter of from 3 to 6 mm were formed. Especially, upon culture of an early state of growth (about 78 hours), a transparent membrane is formed in the periphery of the colonies. The colonies were nontransparent and dark reddish-brown, had a circular shape, and showed a projection state in the form of a pedestal. The rim was entirely fringed, and the shape of the surface was smooth, showing a dry state. IBI-2P mentioned above showed the characteristics of being nitrate ions-utilizable, catalase activity-positive, oxidase activity-positive, diethyl phosphonate-utilizable, degreasing agent-containing waste liquid (for example, plating waste liquid)-utilizable, glucose-fermentable, minomycin-sensitive, gentamicin-sensitive, latamoxef-sensitive, imipenum-sensitive, ampicillin-resistant, cephalocin-resistant, fosfomycin-resistant, not producing any acids from glucose in a medium containing a peptone, and the like. In addition, IBI-2P mentioned above was peritrichous, and had motility. Further, IBI-2 mentioned above had excellent denitrification property and acted on the removal of a nitrogen-containing compound.

In addition, the nucleotide sequence of 16S rDNA of IBI-2P mentioned above was the nucleotide sequence as shown in SEQ ID NO: 1. It was suggested from the homology of the sequence to the above nucleotide sequence that IBI-2P mentioned above is a bacterium belonging to the genus *Alcaligenes*, specifically *Alcaligenes faecalis*. In addition, it was suggested from the results of the phylogenic analysis that IBI-2P mentioned above was a bacterium closely related to *Alcaligenes pacifica, Alcaligenes aquamarina* and *Alcaligenes venustus*.

IBI-3P mentioned above was a gram-negative, aerobic bacterium, which was a *bacillus* having a size of 0.2–0.3×0.5 μm. When IBI-3P mentioned above was cultured on the Columbia agar base at 30° C. for 3 days, colonies of a size having a diameter of from 3 to 5 mm were formed. The colonies were nontransparent and greenish yellow, had a circular shape, and showed a projection state in the form of a half lens. The rim was entirely fringed, and the shape of the surface was smooth, showing a viscous state. IBI-3P mentioned above showed the characteristics of being denitrifiable, degreasing agent-containing waste liquid (for example, plating waste liquid)-utilizable, capable of removing phosphoric acid from the degreasing agent-containing waste liquid by accumulating a phosphoric acid compound in the form of a sphingophospholipid, and the like. IBI-3P served to remove phosphoric acid from the waste liquid, and concurrently degrade and remove a substance that influences a BOD value.

In addition, the nucleotide sequence of 16S rDNA of IBI-3P mentioned above was the nucleotide sequence as shown in SEQ ID NO: 2. It was suggested from the homology of the sequence to the above nucleotide sequence that IBI-3P mentioned above is a bacterium belonging to the genus *Sphingobacterium*. In addition, the nucleotide sequence of 16S rDNA of IBI-3P had a homology of 95% with a nucleotide sequence from *Sphingobacterium faecium*, 95% with a nucleotide sequence of *Sphingobacterium spiritivorum*, 94% with a nucleotide sequence of *Sphingobacterium multivorum*, and 94% with a nucleotide sequence of *Sphingobacterium mizutae*.

IBI-6P mentioned above was a gram-negative, aerobic bacterium, which was a bacterium having a size of 0.3×3-5 μm. When IBI-6P mentioned above was cultured on the Columbia agar base at 30° C. for 3 days, colonies of a size having a diameter of from 5 to 8 mm were formed. In addition, the colonies were nontransparent and pale yellow, had a circular shape, and showed a projection state in the form of a half lens. The rim was entirely fringed, and the shape of the surface was smooth, showing a viscous state. IBI-6P mentioned above showed the characteristics of being catalase activity-positive, oxidase activity-positive, nitrate ions-utilizable, degreasing agent-containing waste liquid (for example, plating waste liquid)-utilizable, reduction-degradable of chlorine-containing compounds, denitrifiable, reducible iron, and the like. In addition, IBI-6P showed the characteristics of a halophilic bacterium (for example, having a high-temperature property, a low water activity, a cell membrane developed with an action of an anti-porter, which is an opposing transport of ions, a thermostable enzyme or the like, and the like). In addition, IBI-6P showed the characteristic of removing a nitrogen-containing compound and a chlorine-containing compound from the waste liquid.

In addition, the nucleotide sequence of 16S rDNA of IBI-6P mentioned above was the nucleotide sequence as shown in SEQ ID NO: 3. It was suggested from the homology of the sequence to the above nucleotide sequence and the phylogenic analysis that IBI-6P mentioned above is *Shewanella algae*.

IBI-15P mentioned above was a gram-negative, aerobic bacterium, which was a bacterium having a size of 0.1×5 μm. When IBI-15P mentioned above was cultured on the Columbia agar base at 30° C. for 3 days, colonies of a size having a diameter of from 3 to 7 mm were formed. In addition, the colonies were semitransparent and pale brown, had a circular shape, and showed a projection state in the form of a half lens. The rim was entirely fringed, and the shape of the surface was mucoid, showing a viscous state. IBI-15P mentioned above showed the characteristics of being oxidase activity-positive, nitrate ion-reducible, growing in a degreasing agent-containing waste liquid (for example, plating waste liquid), denitrifiable, various organic substances (for example, isopropanol, ethanol, diethyl ether, dibenzofuran, and the like)-degradable, sulfide foul odor substance (for example, hydrogen sulfide, and the like)-absorbable, and the like. In addition, IBI-15P mentioned above assimilates an organic substance under unaerobic bright conditions (the photosynthesis reaction (utilizing light) under the conditions where oxygen is absent and light is present), and degrades an organic substance under unaerobic dark conditions (breathing (utilizing oxygen) under the conditions where oxygen is present and light is absent). In other words, according to IBI-15P mentioned above, it can be seen that an effect of disappearing an organic substance-foul odor substance under the conditions where the organic substance is present is exhibited. In addition, IBI-15P mentioned above showed the characteristic of removing a nitrogen-containing compound and phosphoric acid from the waste liquid.

In addition, the nucleotide sequence of 16S rDNA of IBI-15P mentioned above was the nucleotide sequence as shown in SEQ ID NO: 4. It was suggested from the homology of the sequence to the above nucleotide sequence that IBI-15P mentioned above is a bacterium belonging to the genus *Rhodobacter*. Here, the nucleotide sequence of 16S rDNA of IBI-15P had a homology of 98% with a nucleotide sequence from *Rhodobacter litoralis*, 96% with a nucleotide sequence of *Rhodobacter veldkampii*, 96% with a nucleotide sequence of *Rhodobacter massiliensis*, 95% with a nucleotide sequence of *Rhodobacter sphaeroides, and* 94% with a nucleotide sequence of *Rhodobacter azotoformans*.

IBI-40P mentioned above was a gram-positive, aerobic bacterium, which was a coccus having a size of 1.5 to 2 μm. When IBI-40P mentioned above was cultured on the Columbia agar base at 30° C. for 3 days, colonies of a size having a diameter of from 3 to 5 mm were formed. In addition, the colonies were pale green, had a circular shape, and showed a projection state in the form of a half lens. The rim was entirely fringed, and the shape of the surface was smooth, showing a dry state. IBI-40P mentioned above showed the characteristics of being oxidase activity-positive, degreasing agent-containing waste liquid (for example, plating waste liquid)-utilizable, and the like. In addition, IBI-40P mentioned above degrades an organic substance by utilizing oxygen as an oxidizing agent under aerobic conditions, and reduces nitric acid to generate nitrogen by utilizing nitric acid as an oxidizing agent upon degradation of an organic substance under unaerobic conditions. In addition, IBI-40P mentioned above showed polar hydrocarbon (for example, a higher alcohol having 10 to 22 carbon atoms)-utilizability, a higher hydrocarbon having 15 to 20 carbon atoms-utilizability, and a polycyclic aromatic hydrocarbon-utilizability. In addition, IBI-40P mentioned above degraded various kinds of ester compounds (for example, Tween 80 (trade name), and the like).

In addition, the nucleotide sequence of 16S rDNA of IBI-40P mentioned above was the nucleotide sequence as shown in SEQ ID NO: 5. It was suggested from the homology of the sequence to the above nucleotide sequence and the phylogenic analysis that IBI-40P mentioned above is *Micrococcus luteus*.

IBI-6 mentioned above was a gram-negative, aerobic bacterium, which was a coccus having a size of 0.2 to 0.4 μm (or 0.2-0.4×0.4-0.5 nm). When IBI-6 mentioned above was cultured on the Columbia agar base at 30° C. for 3 days in the presence of a very small amount (0.01% by weight) of DMSO, colonies of a size having a diameter of from 3 to 7 mm were formed. In addition, the colonies were semitransparent and pale pink, had a circular shape, and showed a projection state in the form of a half lens. The rim was entirely fringed, and the shape of the surface was smooth, showing a viscous state. Further, IBI-6 mentioned above showed the characteristics of being oxidase activity-positive, catalase activity-positive, denitrifiable, degreasing agent-containing waste liquid (for example, plating waste liquid)-utilizable, accelerating growth in the presence of DMSO, accumulating polyhydroxyalkanoate (PHA) into bacteria, and the like. In addition, IBI-6 mentioned above degraded a substance and a sulfur-containing compound influencing a BOD value.

In addition, the nucleotide sequence of 16S rDNA of IBI-6 mentioned above was the nucleotide sequence as shown in SEQ ID NO: 6. It was suggested from the homology of the sequence to the above nucleotide sequence that IBI-6 mentioned above is a bacterium belonging to the genus *Paracoccus*. Here, the nucleotide sequence of 16S rDNA of IBI-6 had a homology of 99% with a nucleotide sequence from *Paracoccus denitrificans*, 99% with a nucleotide sequence of *Paracoccus pantotrophus*, 99% with a nucleotide sequence of *Paracoccus thiophilus*, and 99% with a nucleotide sequence of *Paracoccus verustus*.

COMPARATIVE EXAMPLE 1

The organic substance-containing waste liquid was treated in the same manner as in EXAMPLE 1, using the same activated sludge and the organic substance-containing waste liquid as in EXAMPLE 1, except that the amount of dissolved oxygen was set at 0.5 to 1.5 mg/L, and that the oxidation-reduction potential was not controlled. After the treatment, the BOD, the COD, the total nitrogen content, and the total phosphorus content of the treated water were determined in the same manner as in EXAMPLE 1.

As a result, the BOD was about 200 ppm, the COD was about 500 mg/L, the total nitrogen content was about 260 mg/L, and the total phosphorus content was about 80 mg/L, showing low decrease ratios of the BOD and the COD, and low removal ratios of nitrogen and phosphorus, as compared to the case of EXAMPLE 1.

COMPARATIVE EXAMPLE 2

The degreasing agent-containing waste liquid was treated in the same manner as in EXAMPLE 1, using the same activated sludge and the degreasing agent-containing waste liquid as in EXAMPLE 1, except that the amount of dissolved oxygen was set at 0.5 to 1.5 mg/L, that the oxidation-reduction potential was not controlled, and a bacterium belonging to the genus *Bacillus* was used in place of the activated sludge. After the treatment, the BOD, the COD, the total nitrogen content, and the total phosphorus content of the treated water were determined in the same manner as in EXAMPLE 1.

As a result, the BOD was about 2,500 mg/L, the COD was about 1,400 mg/L, the total nitrogen content was about 135 mg/L, and the total phosphorus content was about 42 mg/L, showing low decrease ratios of the BOD and the COD, and low removal ratios of nitrogen and phosphorus, as compared to the case of EXAMPLE 1. In addition, as compared to the case of EXAMPLE 1, more time was needed to reach the time period for attaining the standard value under the provision [standards for sewage release of Ogaki-shi [pH: 5.0 to 9.0, BOD (River water release BOD+2×SS): 600 mg/L or less, total nitrogen content: 240 mg/L or less, total phosphorus content: 32 mg/L or less]

EXAMPLE 2

The isolated IBI-2P, IBI-3P, IBI-6P, IBI-15P, IBI-40P, and IBI-6 were separately cultured. Next, the degreasing agent-containing waste liquid was treated in the same manner except that each of the resulting IBI-2P, IBI-3P, IBI-6P, IBI-15P, IBI-40P, and IBI-6 was used in place of the activated sludge in the above EXAMPLE 1.

As a result, after one week, a treated water satisfying the standards for sewage release (BOD: 130 ppm, COD: 245 ppm, total nitrogen: 75 ppm, and total phosphorus: 15 ppm) at a residence time of 42 hours was obtained. Here, the existing ratio of the above IBI-2P to IBI-3P to IBI-6P to IBI-15P to IBI-40P to IBI-6 (ratio of cell count) was almost 1:1:1:1:1:1, so that the existing ratio was stabilized so that the fluctuations by the degreasing agent-containing waste water was 20 to 50 or so for IBI-2P, and 1 to 10 or so for each of the above IBI-3P, IBI-6P, IBI-15P and IBI-40P, based on 100 for IBI-6.

COMPARATIVE EXAMPLE 3

The aeration was carried out in the same manner as in EXAMPLE 1, except that diatomaceous earth, magnesium sulfate, and nutrient broth were not added.

As a result, after 3 to 6 days, the treated water began foaming, thereby making it difficult to continue the treatment, and a foul odor was generated.

EXAMPLE 3

A degreasing agent-containing waste liquid discharged from plating factories and printed factories was treated using an activated sludge as follows.

Here, the degreasing agent-containing waste liquid mentioned above contained at least dipropylene glycol ether, an alkylbenzimidazole, a benzimidazole derivative, diethylene glycol monobutyl ether, monoethanolamine, a polyoctyl phenyl ether, isopropyl alcohol, ethylene glycol, N,N'-dimethylformamide, or the like.

In addition, the biochemical oxygen demand (BOD), the chemical oxygen demand (COD), the total nitrogen content, and the total phosphorus content were respectively determined for the above degreasing agent-containing waste liquid. The above BOD was obtained by measuring an amount of dissolved oxygen in a sample after 5 days of culture and an amount of dissolved oxygen in a sample before the culture using a product under the trade name of DO meter OM 12 (manufactured by HORIBA, Ltd.), and calculating the BOD on the bases of the numerical values of the amounts of dissolved oxygen obtained before and after the culture. The above COD was evaluated by measuring an amount of oxygen chemically consumed using potassium permanganate. The above total nitrogen content was evaluated by adding sodium hydroxide and potassium peroxodisulfate to the degreasing agent-containing waste liquid, heating the resulting mixture at 120° C. for 30 minutes, and adding hydrochloric acid to product obtained, and determining the absorbance of the resulting product at 220 nm in accordance with the ultraviolet absorbance photometry. The above total phosphorus content was evaluated in accordance with nitric acid-sulfuric acid degradation method by adding nitric acid to the degreasing agent-containing waste liquid, heating the mixture to concentrate, thereafter adding nitric acid and sulfuric acid to a product obtained, heating the mixture to convert a phosphorus-containing compound to a phosphate ion, and to concurrently degrade an organic substance, and determining phosphate ions in the resulting product with molybdenum blue (reduced with ascorbic acid) absorbance photometry.

As a result, the above degreasing agent-containing waste liquid had a BOD of from about 4,000 to about 6,500 ppm on average, and a COD of from about 3,000 to about 5,000 ppm on average. In addition, the above degreasing agent-containing waste liquid had a total nitrogen content of from about 50 to about 200 ppm on average, and a total phosphorus content of from about 100 to about 250 ppm on average.

In FIG. 2, the above degreasing agent-containing waste liquid was sequentially allowed to pass through, at a flow rate of from 300 to 450 m$^3$/day, a pH adjusting tank (18 m$^3$), an organism ante-relaying tank (98 m$^3$), an aeration tank (referred to as "ante-aeration tank," comprising 4 tanks, total volume: 405 m$^3$), a precipitation tank (44 m$^3$) and an aeration tank ("post-aeration tank," comprising 3 tanks, total volume: 219 m$^3$), and a submerged-membrane equipment.

In the above pH adjustment tank, the pH was adjusted to 6.4 to 7.5 by adding a 32% by weight sodium hydroxide or a 18% by weight sulfuric acid to the introduced degreasing agent-containing waste liquid in a continuous treatment under a pH control. Here, the degreasing agent-containing waste liquid introduced into the above pH adjustment tank was allowed to reside for 5 minutes. During the residence, the pH was adjusted by stirring the above degreasing agent-containing waste liquid with a stirrer (Takeuchi Seisakusho: Model TFGO0203-20) in the pH adjustment tank.

In the above organism ante-relaying tank, the treated water supplied from the above pH adjustment tank was adjusted so that the ORP was from 0 to 50 mv using $H_2O_2$ under the control of ORP.

The above ante-aeration tank comprises a first aeration tank through a fourth aeration tank. At the stage of the beginning of the treatment of the degreasing agent-containing waste liquid, 24,300 kg of the above activated sludge was introduced into the first aeration tank.

In the above ante-aeration tank, the treated water supplied from the above organism ante-relaying tank was contacted with the activated sludge. In the first aeration tank, the aeration was carried out according to air-dissipating type aeration by introducing the air under the condition of an air flow rate of 15.0 kg/h. Also in the second aeration tank, the aeration was carried out by rotating the rotary impellers under the same conditions as in the above first aeration tank. In the third aeration tank, the aeration was carried out while rotating rotary impellers at a rate of 600 rpm. Also in the fourth aeration tank, the aeration was carried out under the same conditions as in the above third aeration tank. Here, in each of the aeration tanks, the amount of dissolved oxygen was monitored with DO meter OM 12 (trade name) (manufactured by HORIBA, Ltd.), and the amount of dissolved oxygen was maintained at a level of 5 to 6 mg/L, which was higher than usually set amount of dissolved oxygen by adjusting the air flow rate or the rotational speed of the rotary impellers.

In the above precipitation tank, solid substances of the activated sludge or the like in the treated water supplied from the above aeration tank were allowed to precipitate. In the precipitation tank, the above activated sludge was fed back to the above aeration tank and at the same time the remainder treated water was supplied into the post-aeration tank.

In the above post-aeration tank, the treated water supplied from the above precipitation tank was contacted with the same activated sludge as in the ante-aeration tank. In the first aeration tank, the air was supplied into the tank from both sides of the bottom of the tank by a diffuser pipe aeration method, and the aeration was carried out by whirling the air inside the tank. In the second aeration tank, the aeration was carried out by supplying the air fed from a blower into a submerged-membrane equipment comprising a flat membrane (trade name: H3-510, manufactured by KUBOTA Corporation). In the third aeration tank, the aeration was carried out by whirling the air inside the tank at a rotation of 600 rpm while introducing the air under the condition of 5.0 Kg/h with an aerator. Here, in each of the aeration tanks, the amount of dissolved oxygen was monitored with DO meter OM 12 (trade name), manufactured by HORIBA, Ltd., and the amount of dissolved oxygen was maintained at a level of 5 to 6 mg/L by adjusting the air flow rate or the rotational speed of the rotary impellers.

The BOD, the COD, the total nitrogen content, and the total phosphorus content were determined for the treated water obtained in the same manner as above. As a result, the BOD was from 10 to 100 ppm, the COD was from 100 to 600 ppm, the total nitrogen content was from 50 to 200 ppm, and the total phosphorus content was from 20 to 50 ppm. In addition, the removal ratios of the BOD, the COD, the total nitrogen content, and the total phosphorus content were 99.5%, 89.2%, 81.7%, and 78.9%, respectively.

EXAMPLE 4

The same degreasing agent-containing waste liquid as in EXAMPLE 3 mentioned above was treated plural times, and thereafter the activated sludge was collected to examine a microorganism existing in the activated sludge.

The above activated sludge was stepwise dilute with sterile physiological saline. Each of the dilutions obtained was spread to a nutrient broth-glucose agar medium [composition: 0.8% by weight Nutrient Broth, manufactured by Oxoid), Catalog No.: CM-1, 0.8% by weight glucose, 0.6% by weight NaCl, 0.1% by weight dry yeast extract, 1.5% by weight agar, pH 7.0], and cultured at 30° C. until colonies appeared. Thereafter, the colonies of a microorganism were collected from the colonies appeared using the morphology and the color of the colonies as indices. The collected microorganism was spread on Columbia agar base (trade name), and cultured at 30° C. for 3 days. The collection and the culture of the microorganism were repeated until the morphology and the color of the colonies became even.

Next, in accordance with an ordinary method (a method described in the Reference Book), gram staining, oxidase test, and other physiological and biochemical properties for each of the microorganisms obtained were examined. In addition, the morphology and the motility of each of the microorganisms were observed using an optical microscope (attached with Labophoto phase-contrast device (trade name), manufactured by Nihon Kogaku (Nikon Corporation)). Further, a DNA was extracted from each of the microorganisms, and PCR was carried out using a thermal cycler (manufactured by ABI, 2730) with the DNA obtained as a template. The thermal profile of PCR was the conditions of incubating at 94° C. for 1 minute; carrying out 30 cycles of reaction, wherein one cycle consists of 94° C. for 1 minute, 63° C. for 1 minute, and 72° C. for 1.5 minutes; incubating at 72° C. for 2 minutes; and thereafter at 4° C. The resulting product was mixed with a PEG (Poly Ethylene Glycol: manufactured by Wako Pure Chemical Industries, Ltd.)/NaCl solution (30% (W/V)), and the mixture obtained was allowed to stand at 4° C. for 30 minutes to 1 hour. Thereafter, the mixture obtained was centrifuged at 11,000×g (14,000 rpm) for 10 minutes at room temperature, and the supernatant was removed. One milliliter of a 70% by weight chilled ethanol was added to the resulting product, and the mixture was centrifuged at 11,000×g (14,000 rpm) for 1 minute, the supernatant was discarded, and the residue was dried for 5 minutes. Twenty microliters of sterile purified water was added to the resulting product. The nucleotide sequence of the resulting product was determined using a kit manufactured by ABI under the trade name of BIG-DYE® Terminator V 3.1 Cycle Sequencing Kit. The determined nucleotide sequence was analyzed for homology with the data of the nucleotide sequences in the DDBJ and NCBI Data Base. In the analysis based on the Data Base, the setting conditions for the parameters in the Blast search (Fasta) program are default conditions, i.e. Word Size: 11, Cost to open a gap: 0, Cost to extend a gap: 0, X dropoff value for gapped alignment 30, Penalty for a nucleotide mismatch: −3, Reward for a nucleotide match: 1, Threshold for extending hits: 0. In addition, the phylogenic analysis was carried out by calculating alignment on the basis of Clustal X 1.83, and preparing a phylogenic tree with Tree View. The setting conditions of the parameters in the Clustal X were Pairwise parameter (Gap opening 8-12, Gap extension 0.1-0.2), Multialignment parameter (Gap opening 8-12, Delay divergent sequence 15-30%, DNA transition weight 0.2-0.5). Here, when the determined nucleotide sequence had a homology with a nucleotide sequence in the Data Base of 99% or more, it is considered that the microorganism is a microorganism that is identical on a species level to the microorganism serving as an origin of the nucleotide sequence in the Data Base. Further, a phylogenic analysis was carried out and comprehensively judged. In addition, when the determined nucleotide sequence has a homology of 95% or more, the microorganism is a microorganism that is identical on a genus level to the microorganism serving as an origin of the nucleotide sequence in the Data Base. Further, a phylogenic analysis was carried out and comprehensively judged.

As a result, three kinds of bacteria, i.e., IBI-13, IBI-2 and IBI-6 were isolated. This IBI-6 is the same bacterium as IBI-6 mentioned above.

IBI-13 mentioned above was a gram staining-negative, and aerobic. When IBI-13 mentioned above was cultured on Columbia agar base (trade name) (manufactured by BBL, commercial article number: 211124) to which a very small amount (0.05% by weight) of DMSO was added at 30° C. for 4 days, colonies of a size having a diameter of from 3 to 5 mm were formed. The colonies had a color of a pale reddish-brown, a shape of a circular shape, a projection state in the form of a half lens, a rim being entirely fringed, a shape of the surface being smooth, a transparency of nontransparent, and a viscosity of being viscous. Also, the above IBI-13 had a size of 0.2×0.5 μm. Further, IBI-13 mentioned above showed the characteristics of being catalase activity-positive, nitrate ions-utilizable, glucose-utilizable in the presence of DMSO, and degreasing agent-containing plating waste liquid-utilizable. In addition, it could be seen from the results of the nucleotide sequence (SEQ ID NO: 7) of 16S rDNA and the phylogenic analysis that the above IBI-13 is a bacterium closely related to *Bosea thiooxidans*.

IBI-2 mentioned above was a gram staining-negative, and aerobic. When IBI-2 mentioned above was cultured on the Columbia agar base (trade name), to which a very small amount of DMSO was added, at 30° C. for 4 days, colonies of a size having a diameter of from 3 to 4 mm were formed. The colonies had a color of a pale pink, a shape of a circular shape, a projection state in the form of a half lens, a rim being entirely fringed, a shape of the surface being smooth, a transparency of nontransparent, and a viscosity of being viscous. Also, the above IBI-2 was a coccus having a size of 0.4×0.4 μm. Further, IBI-2 mentioned above showed the characteristics of being oxidase activity-positive, catalase activity-positive, denitrifiable, accelerating the growth in the presence of DMSO, and degreasing agent-containing plating waste liquid-utilizable. In addition, it was suggested from the nucleotide sequence (SEQ ID NO: 8) of 16S rDNA that the above IBI-2 is a bacterium belonging to *Paracoccus verustus*. In addition, the nucleotide sequence of 16S rDNA of the above IBI-2 showed a homology of 99% with the nucleotide sequence of *Paracoccus denitrificans*, and 99% with the nucleotide sequence of *Paracoccus pantotrophus*. In addition, the results of the phylogenic analysis were also the same.

Further, IBI-13, IBI-2, and IBI-6 were present in the above activated sludge in an existing ratio of about 4:1:1.

EXAMPLE 5

Each of the isolated IBI-13, IBI-2, and IBI-6 was cultured in the Columbia agar base containing 0.01 to 0.05% by weight DMSO at 30° C., and the cultures obtained were mixed with each other in an amount of 35 mL each of $1 \times 10^{12}$ CFU/mL cell equivalent amount for each culture, to give a mixture.

The pH of the degreasing agent-containing waste liquid discharged from the plating factories and printed factories in the same manner as in EXAMPLE 3 was adjusted to 7.0, and 100 mL of the mixture was added to 350 L of the waste water obtained. Next, the mixture obtained was treated in a manner that the residence time was 36 hours at 17° to 25° C., while maintaining the amount of dissolved oxygen to 3 to 6 mg/L.

Thereafter, the solid substances and the bacteria were removed from the mixture obtained by a membrane treatment. The BOD, the COD, the total nitrogen content, and the total phosphorus content for the treated water obtained were determined in the same manner as in EXAMPLE 3.

As a result, the treated water having a BOD of 50 mg/L, a COD of 230 mg/L, a total nitrogen of 120 mg/L, and a total phosphorus of 20 mg/L was obtained.

COMPARATIVE EXAMPLE 4

The treatment was maintained under the same conditions as in EXAMPLE 3 using IBI-13, IBI-2, and IBI-6, under the condition of DO 0.1 mg/L. As a result, the mixture was foamed, thereby making difficult to carry out the treatment of a waste liquid.

EXAMPLE 6

The isolated IBI-2P, IBI-3P, IBI-6P, IBI-15P, IBI-40P, IBI-2, IBI-13 and IBI-6 were separately cultured. Next, the organic substance-containing waste liquid was treated with the treatment facilities in FIG. 1 in the same manner, except that IBI-2P, IBI-3P, IBI-6P, IBI-15P, IBI-40P, IBI-2, IBI-13, and IBI-6 obtained were used in place of the activated sludge in EXAMPLE 1.

As a result, after one week, a treated water satisfying standards of sewage release (BOD: 130 ppm, COD: 245 ppm, total nitrogen: 75 ppm, total phosphorus content: 15 ppm) was obtained. Here, the existing ratio of IBI-2P to IBI-3P to IBI-6P to IBI-15P to IBI-40P to IBI-2 to IBI-13 to IBI-6 (ratio of cell count) was about 1:1:1:1:1:1:1:1, and the existing ratio was stability to an extent that fluctuations were found by the organic substance containing-waste liquid of 20 to 50 or so for IBI-2P; 1 to 10 for IBI-3P, IBI-6P, IBI-15P and IBI-40P, 40 to 100 for IBI-2, and 100 or so for IBI-13, based on 100 of IBI-6.

EXAMPLE 7

Each of the isolated IBI-2P, IBI-3P, IBI-6P, IBI-15P, IBI-40P, IBI-2, IBI-13 and IBI-6 was cultured in the Columbia agar base containing 0.01 to 0.05% by weight of DMSO at 30° C., and the cultures obtained were mixed with each other in an amount of 35 mL each of $1\times10^{12}$ CFU/mL cell equivalent amount for each culture, to give a mixture.

In the treatment facilities of FIG. 1, the pH of the degreasing agent-containing waste liquid discharged from the plating factories and printed factories in the same manner as in EXAMPLE 1 was adjusted to 7.0, and 100 mL of the mixture was added to 350 L of the waste water obtained. Next, the mixture obtained was treated in a manner that the residence time was 36 hours at 25° to 45° C., while maintaining the amount of dissolved oxygen to 3 to 6 mg/L.

Thereafter, the solid substances and the bacteria were removed from the mixture obtained by a membrane treatment. The BOD, the COD, the total nitrogen content, and the total phosphorus content for the treated water obtained were determined in the same manner as in EXAMPLE 1.

As a result, the treated water having a BOD of 50 mg/L, a COD of 230 mg/L, a total nitrogen of 120 mg/L, and a total phosphorus of 20 mg/L was obtained.

EXAMPLE 8

Each of the isolated IBI-2P, IBI-3P, IBI-6P, IBI-15P, IBI-40P, IBI-2, IBI-13 and IBI-6 was cultured in the Columbia agar base containing 0.01 to 0.05% by weight of DMSO at 30° C., and the cultures obtained were mixed with each other in an amount of 35 mL each of $1\times10^{12}$ CFU/mL cell equivalent amount for each culture, to give a mixture.

In the treatment facilities of FIG. 1, the pH of the degreasing agent-containing waste liquid discharged from the food processing factories in the same manner as in EXAMPLE 1 was adjusted to 5.0, and 100 mL of the mixture was added to 350 L of the waste water obtained. Next, the mixture obtained was treated in a manner that the residence time was 36 hours at 15° to 30° C., while maintaining the amount of dissolved oxygen to 3 to 6 mg/L.

Thereafter, the solid substances and the bacteria were removed from the mixture obtained by a membrane treatment. The BOD, the COD, the total nitrogen content, and the total phosphorus content for the treated water obtained were determined in the same manner as in EXAMPLE 1.

As a result, the treated water having a BOD of 20 mg/L or less, a COD of 20 mg/L or less, a total nitrogen of 1 mg/L or less, and a total phosphorus of 1 mg/L or less was obtained.

EXAMPLE 9

Using an apparatus for treating waste water comprising as one system a 0.9 M³ aeration tank composed of 4 tanks (first to fourth aeration tanks), a 1.5 M³ precipitation tank composed of 1 tank, and a 1.7 M³ concentrated sludge tank composed of 1 tank, wherein the DO of each aeration tank was from 2 to 8 mg/l, and a sludge feed-back was from 2Q to 3.5Q, the operation was carried out for sewage, domestic waste water, and waste water from biology laboratories as raw sewages by introducing the raw sewage at a water temperature of 5° C. for 5 to 5.8 M³/day (retention time: 15 to 17 hours) (Test A). Also, the operation was similarly carried out at a water temperature of 23° to 25° C. at a raw sewage feeding rate of from 10 to 12 M³/day (residence time: 7.2 to 8.6 hours) (Test B). Further, as a control, the operation was similarly carried out at a water temperature of 14° to 17° C. at a raw sewage feeding rate of from 7 to 9.5 M³/day (residence time: 9 to 12 hours) (Test C).

In Test A, bulking takes place on the third to fifth day after the beginning of the operation, so that the sludge was allowed to cause liquid-solid separation to be suspended. The suspending sludge caused by bulking covered the surface in the precipitation tank, a foul odor was generated and gradually solidified to form a scum. In the aeration tank, the sludge is also solidified after additional 7 days, so that the generation of scum was found (MLSS (suspended substance in tank water): 7000 to 9000 mg/l). In addition, in Test B, the foaming takes place on the fifteenth day after the beginning of the operation, and the sludge was suspended together with foam in the aeration tank and the sludge concentration tank, to give a bulking state. The thickness of this sludge was from 10 to 15 cm, and the formation of scum was found (MLSS: 7000 to 9000 mg/l). On the other hand, in Test C used as a control, the generation of scum was not found.

In view of the above, in Test A and Test B, 80 g of DL-alanine and 800 g of magnesium sulfate (anhydride) were dissolved in 100 liters of water, and 50 g of phenol was added thereto for preventing corrosion, to give an activated liquid (A). One-hundred liters of this activated liquid was added to a first aeration tank with a constant-volume pump over a period of 16 to 20 days (5 to 6.5 L/days). As a result, the generated disappeared in fourth to seventh days, to give a clear supernatant in a precipitation tank (In Test A, the treated water had a BOD of from 10 to 18 mg/L, and in Test B, the treated water had a BOD of from 5 to 12 mg/L.) Hereinafter, the generation of scum did not take place during the subsequent 6-month operation even at the season changes.

EXAMPLE 10

The waste water treatment was carried out as in Test B in accordance with EXAMPLE 9. On the fifteenth day, the suspension of the sludge was found in a thickness of from 10 to 15 cm in an upper layer of the treated water, so that the activated liquid (A) prepared in EXAMPLE 9 was continuously added to a first tank, and that also fine volcanic rock powder was also added to the first tank once a day in an amount of 10 g/day. As a result, the generated scum disappeared in three days, and the scum was not generated at all during the subsequent 6-month operation.

EXAMPLE 11

The waste water treatment was carried out as in Test B in accordance with EXAMPLE 9. On the thirteenth day, the suspension of the sludge was found in a thickness of from 10 to 15 cm in an upper layer of the treated water. Therefore, 40 g of Nutrient Broth and 800 g of magnesium sulfate (anhydride) were dissolved in 100 liters of water in place of DL-alanine, and 50 g of phenol was added to the solution obtained, to prepare 100 L of an activated liquid (C). The activated liquid (C) was added to the first aeration tank in 20 days. As a result, a bulking state was eliminated after 4 days.

EXAMPLE 12

The waste water treatment was carried out as in Test B in accordance with EXAMPLE 9. An unexpected abnormal situation that the raw sewage containing the sludge was introduced was generated during the test, and the suspension of the sludge was found in the aeration tank, the precipitation tank, and the concentrated sludge tank a half day later (thickness: 15 to 20 cm). Eighty grams of DL-alanine, 40 g of Nutrient Broth (80 g), and 800 g of magnesium sulfate (anhydride) were dissolved in 100 L of water, and 50 g of phenol was added thereto for preventing corrosion, to give an activated liquid (D). One-hundred liters of this activated liquid was added to a first aeration tank with a constant-volume pump. Concurrently, a fine obsidian powder was added to the first aeration tank at a rate of 10 g/day once a day. Notwithstanding the introduction of the sludge, the suspended sludge disappeared after 6 days, to give a clear supernatant in the precipitation tank (BOD of treated water: 16 mg/L).

The invention claimed is:

1. A method of treating an organic substance containing waste liquid, comprising:
   contacting an organic substance containing waste liquid and an activated sludge to produce a mixture, wherein said activated sludge comprises bacteria from
   (i) an *Alcaligenes* selected from the group consisting of *Alcaligenes faecalis, Alcaligenes pacifica, Alcaligenes aquamarina* and *Alcaligenes venustus*,
   (ii) a *Sphingobacterium* selected from the group consisting of *Sphingobacterium faecium, Sphingobacterium spiritivorum, Sphingobacterium multivorum*, and *Sphingobacterium mizutae*,
   (iii) *Shewanella algae*,
   (iv) a *Rhodobacter* selected from the group consisting of *Rhodobacter litoralis, Rhodobacter veldkampii, Rhodobacter massiliensis, Rhodobacter sphaeroides*, and *Rhodobacter azotoformans*,
   (v) *Micrococcus luteus*,
   (vi) a *Paracoccus* selected from the group consisting of *Paracoccus denitrificans, Paracoccus pantotrophus*, and *Paracoccus thiophilus*,
   (vii) *Bosea thiooxidans*, and
   (viii) *Paracoccus verustus*, wherein the *Alcaligenes* is bacterial strain IBI-2P, Accession No. FERM BP-10565, the *Sphingobacterium* is bacterial strain IBI-3P, Accession No. FERM BP-10566, the *Shewanella algae* is bacterial strain IBI-6P, Accession No. FERM BP-10568, the *Rhodobacter* is bacterial strain IBI-15P, Accession No. FERM BP-10570, the *Micrococcus luteus* is bacterial strain IBI-40P, Accession No. FERM BP-10571, the *Paracoccu* is bacterial strain IBI-6, Accession No. FERM BP-10567, the *Bosea thiooxidans* is bacterial strain IBI-13 designated as Accession No. FERM BP-10569, and the *Paracoccus verustus* is bacterial strain IBI-2, Accession No. FERM BP-10564.

2. The method of claim 1, wherein the organic substance containing waste liquid is a waste liquid containing at least one compound selected from the group consisting of higher alcohols, sulfide compounds, alkylthiosulfate compounds, nitrogen containing alkyl compounds, phosphoric acid compounds, diethylene glycol monobutyl ether, dipropylene glycol ether, monoethanolamine, polyoctyl phenyl ethers having an average molecular weight of from 696 to 872, isopropyl alcohol, ethylene glycol, N,N'-dimethylformamide, and benzimidazoles having an alkyl group having 1 to 4 carbon atoms.

3. The method of claim 1, wherein the organic substance containing waste liquid is raw sewage, domestic waste water, waste water from a food-processing factory, or a degreasing agent containing waste liquid.

4. The method of claim 1, wherein said mixture has dissolved oxygen (DO) content of from 2 to 8 mg/L.

5. The method of claim 1, further comprising adding a magnesium compound, a silicon containing compound and a nutritional supplement for cell culture to said mixture.

6. The method of claim 1, wherein the organic substance containing waste liquid has an original waste water with a pH of from 3.5 to 8.5.

7. The method of claim 1, wherein said mixture has a pH of from 6.0 to 9.0 or is adjusted to have a pH from 6.0 to 9.0.

8. The method of claim 1, wherein said mixture has an oxidation-reduction potential (ORP) inside a treatment tank of from −100 to 150 mv or is adjusted to an ORP of from −100 mv to 150 mv.

9. The method of claim 1, wherein said mixture has a temperature of from 10° to 60° C.

10. The method of any one of claims 1 to 9, wherein the organic substance containing waste liquid is previously subjected to a step of removing a metal.

11. The method of any one of claims 1 to 9, wherein a resulting waste liquid from said mixture is then filtered with a submerged membrane.

12. An apparatus for treating an organic substance containing waste liquid in accordance with the method of any one of claims 1 to 9 comprising:
   (a) a treatment tank containing an activated sludge comprising the bacteria
   (i) an *Alcaligenes* selected from the group consisting of *Alcaligenes faecalis, Alcaligenes pacifica, Alcaligenes aquamarina* and *Alcaligenes venustus*,
   (ii) a *Sphingobacterium* selected from the group consisting of *Sphingobacterium faecium, Sphingobacterium spiritivorum, Sphingobacterium multivorum*, and *Sphingobacterium mizutae*,
   (iii) *Shewanella algae*,
   (iv) a *Rhodobacter* selected from the group consisting of *Rhodobacter litoralis, Rhodobacter veldkampii, Rhodobacter massiliensis, Rhodobacter sphaeroides*, and *Rhodobacter azotoformans*,
   (v) *Micrococcus luteus*,
   (vi) a *Paracoccus* selected from the group consisting of *Paracoccus denitrificans, Paracoccus pantotrophus*, and *Paracoccus thiophilus*, (vii) *Bosea thiooxidans*, and
(viii) *Paracoccus verustus*; and
(b) a means of filtering a waste liquid in the treatment tank with a submerged-membrane.

13. An apparatus for treating an organic substance-containing waste liquid in accordance with claim 10 which comprises
(a) a treatment tank containing an activated sludge comprising bacteria of
(i) an *Alcaligenes* species selected from the group consisting of *Alcaligenes faecalis, Alcaligenes pacifica, Alcaligenes aquamarina* and *Alcaligenes venustus*,
(ii) a *Sphingobacterium* species selected from the group consisting of *Sphingobacterium faecium, Sphingobacterium spiritivorum, Sphingobacterium multivorum*, and *Sphingobacterium mizutae*,
(iii) *Shewanella algae*,
(iv) a *Rhodobacter* species selected from the group consisting of *Rhodobacter litoralis, Rhodobacter veldkampii, Rhodobacter massiliensis, Rhodobacter sphaeroides*, and *Rhodobacter azotoformans*,
(v) *Micrococcus luteus*,
(vi) a *Paracoccus* species selected from the group consisting of *Paracoccus denitrificans, Paracoccus pantotrophus*, and *Paracoccus thiophilus*,
(vii) *Bosea thiooxidans*, and
(viii) *Paracoccus verustus*; and
(b) a means of filtering a waste liquid in the treatment tank with a submerged membrane.

14. An apparatus for treating an organic substance containing waste liquid in accordance with claim 11 which comprises
(a) a treatment tank containing an activated sludge comprising bacteria of
(i) an *Alcaligenes* species selected from the group consisting of *Alcaligenes faecalis, Alcaligenes pacifica, Alcaligenes aquamarina* and *Alcaligenes venustus*,
(ii) a *Sphingobacterium* species selected from the group consisting of *Sphingobacterium faecium, Sphingobacterium spiritivorum, Sphingobacterium multivorum*, and *Sphingobacterium mizutae*,
(iii) *Shewanella algae*,
(iv) a *Rhodobacter* species selected from the group consisting of *Rhodobacter litoralis, Rhodobacter veldkampii, Rhodobacter massiliensis, Rhodobacter sphaeroides*, and *Rhodobacter azotoformans*,
(v) *Micrococcus luteus*,
(vi) a *Paracoccus* species selected from the group consisting of *Paracoccus denitrificans, Paracoccus pantotrophus*, and *Paracoccus thiophilus*,
(vii) *Bosea thiooxidans*, and
(viii) *Paracoccus verustus*; and
(b) a means of filtering a waste liquid in the treatment tank with a submerged membrane.

* * * * *